United States Patent
Favreau et al.

(10) Patent No.: US 9,644,011 B2
(45) Date of Patent: May 9, 2017

(54) MU-CONOTOXIN PEPTIDES AND USE THEREOF AS A LOCAL ANESTHETIC

(71) Applicants: Philippe Favreau, Amancy (FR); Evelyne Benoit, Gif-sur-Yvette (FR); Jordi Molgo, Gif-sur-Yvette (FR); Reto Stöcklin, Bernex (CH)

(72) Inventors: Philippe Favreau, Amancy (FR); Evelyne Benoit, Gif-sur-Yvette (FR); Jordi Molgo, Gif-sur-Yvette (FR); Reto Stöcklin, Bernex (CH)

(73) Assignee: CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 0 days.

(21) Appl. No.: 13/739,321

(22) Filed: Jan. 11, 2013

(65) Prior Publication Data
US 2013/0203676 A1 Aug. 8, 2013

Related U.S. Application Data

(63) Continuation of application No. 12/084,572, filed as application No. PCT/IB2006/003147 on Nov. 8, 2006, now abandoned.

(60) Provisional application No. 60/734,267, filed on Nov. 8, 2005.

(51) Int. Cl.
*A61K 38/17* (2006.01)
*C07K 14/435* (2006.01)

(52) U.S. Cl.
CPC .... *C07K 14/43504* (2013.01); *A61K 38/1767* (2013.01)

(58) Field of Classification Search
CPC .... A61K 38/08; A61K 38/10; A61K 38/1767; C07K 7/06; C07K 7/08; C07K 14/43504
See application file for complete search history.

(56) References Cited

U.S. PATENT DOCUMENTS

| | | | |
|---|---|---|---|
| 4,081,533 A * | 3/1978 | Cheesman | C07K 5/0823 514/10.1 |
| 4,952,574 A * | 8/1990 | Banitt | C07D 213/40 514/315 |
| 5,670,622 A | 9/1997 | Shon et al. | 530/324 |
| 6,077,822 A * | 6/2000 | Dyrsting | A61K 31/66 514/2.4 |
| 2003/0050234 A1 | 3/2003 | Olivera et al. | 514/12 |
| 2012/0087969 A1 | 4/2012 | Favreau et al. | 424/422 |

FOREIGN PATENT DOCUMENTS

WO  WO 02/07678  1/2002
WO  WO 2004/099238  11/2004

OTHER PUBLICATIONS

Favreau et al. A novel mu-conopeptide, CnIIIC, exerts potent and preferential inhibition . . . British Journal of Pharmacology. 2012, vol. 166, pp. 1654-1668.*
Favreau et al. Biochemical Characterization and Nuclear Magnetic Resonance Structure of Novel alpha-Conotoxins Isolated from the Venom of Conus consors. Biochemistry. 1999, vol. 38, pp. 6317-6326.*
Armishaw, C., et al. (2005), "Conotoxins as research tools and drug leads", *Current Protein and Peptide Science*, 6: 221-240.
Bulaj, G., et al. (2005), "Novel conotoxins from *Conus striatus* and *Conus kinoshitai* selectively block TTX-resistant sodium channels", *Biochemistry*, 44: 7259-7265.
West, P., et al. (2002), "μ-conotoxin SmIIIA, a potent inhibitor of tetrodotoxin-resistant sodium channels in amphibian sympathetic and sensory neurons", *Biochemistry*, 41: 15388-15393.
International Search Report dated Mar. 1, 2007 issued in PCT Application No. PCT/IB2006/003147.
International Preliminary Report on Patentability dated May 14, 2008 issued in PCT Application No. PCT/IB2006/003147.
Office Action dated Jul. 12, 2011 issued in U.S. Appl. No. 12/084,572.
Office Action dated Jan. 12, 2012 issued in U.S. Appl. No. 12/084,572.
Office Action dated Jul. 11, 2012 issued in U.S. Appl. No. 12/084,572.

\* cited by examiner

*Primary Examiner* — Jeffrey E Russel
(74) *Attorney, Agent, or Firm* — Harness, Dickey & Pierce, P.L.C.

(57) ABSTRACT

The present invention relates to novel mu-conotoxin peptides, biologically active fragments thereof, combinations thereof and/or variants thereof. The invention also relates to their use in pharmaceutical composition for the treatment or prevention of pain, and their use in the preparation of an anesthetic.

33 Claims, 15 Drawing Sheets

FIG. 3 A

Control          0.1 μM          0.3 μM          0.6 μM 0.2 N
0.1 s

FIG. 3 B $A_{PhF} / A_C = 1 / [ 1 + ([conotoxin\ CnIIIA] / K_D)^{nH} ]$ $K_D = 0.15\ \mu M$

[conotoxin CnIIIA] (μM)

Relative contraction amplitude

FIG. 5 A
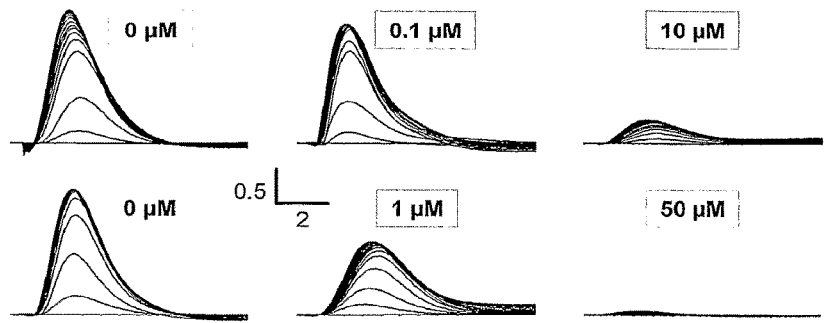
FIG. 5 B
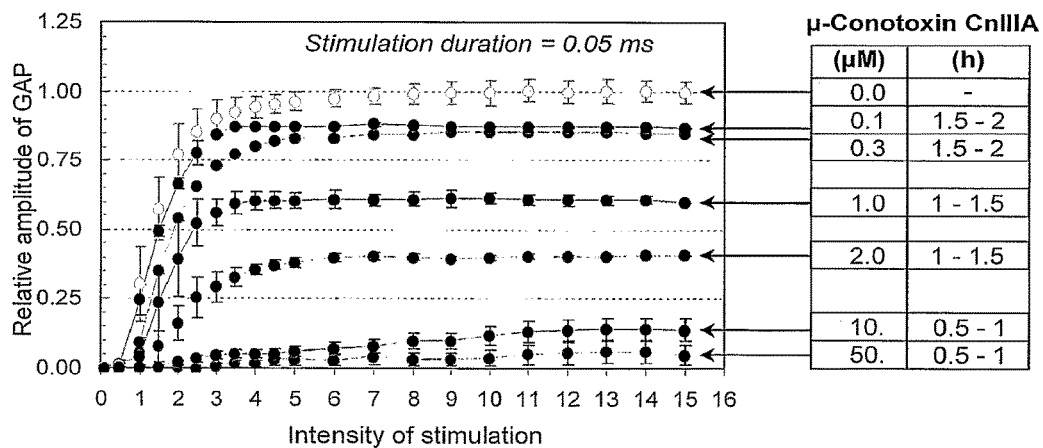
FIG. 5 C
| Concentration | 0 µM | 0.1 µM | 0.3 µM | 1 µM | 2 µM | 10 µM | 50 µM |
|---|---|---|---|---|---|---|---|
| Relative GAP [1] | 1.00 ± 0.00 (n = 6) | 0.87 ± 0.05 (n = 2) | 0.85 ± 0.00 (n = 1) | 0.60 ± 0.11 (n = 4) | 0.41 ± 0.08 (n = 3) | 0.14 ± 0.06 (n = 3) | 0.05 ± 0.03 (n = 3) |
| $V_{50\%}$ (V) [2] | 1.40 ± 0.20 (n = 6) | 1.38 ± 0.13 (n = 2) | 1.75 ± 0.00 (n = 1) | 1.81 ± 0.32 (n = 4) | 2.25 ± 0.41 (n = 3) | 5.50 ± 0.00 (n = 1) | 4.25 ± 0.00 (n = 1) |
| Relative velocity | 1.00 ± 0.00 (n = 6) | 1.15 ± 0.17 (n = 2) | 0.97 ± 0.00 (n = 1) | 1.06 ± 0.23 (n = 4) | 1.02 ± 0.14 (n = 3) | 1.03 ± 0.14 (n = 3) | 1.09 ± 0.24 (n = 2) |

FIG. 6

[Graph: Relative amplitude of PAG vs [mu-conotoxin CnIIIA] (µM); $n_H = 1.02$ ($r^2 = 0.997$); $K_D = 1.53\ \mu M$]

FIG. 8 A
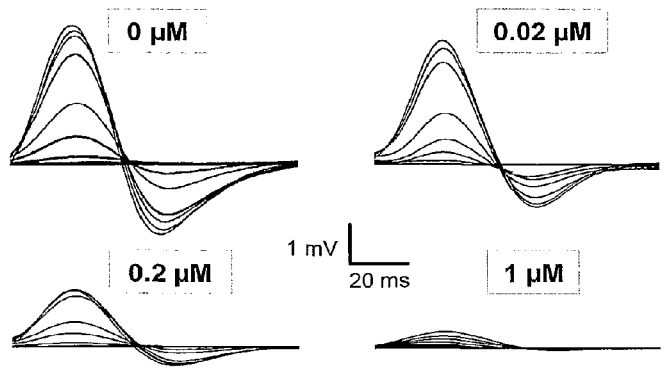
FIG. 8 B
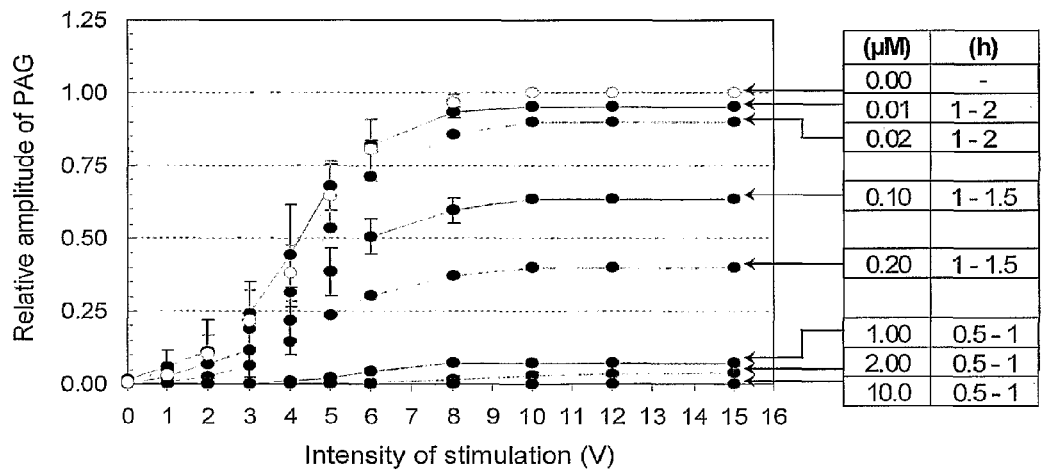
FIG. 8 C
| Concentration | 0 µM | 0.01 µM | 0.02 µM | 0.1 µM | 0.2 µM | 1 µM | 2 µM | 10 µM |
|---|---|---|---|---|---|---|---|---|
| Relative GAP [1] | 1.00 ± 0.00 (n = 6) | 0.95 ± 0.03 (n = 2) | 0.90 ± 0.00 (n = 1) | 0.64 ± 0.13 (n = 3) | 0.40 ± 0.00 (n = 1) | 0.07 ± 0.03 (n = 3) | 0.04 ± 0.03 (n = 3) | 0.00 ± 0.00 (n = 1) |
| $V_{50\%}$ (V) [2] | 4.58 ± 0.37 (n = 6) | 4.63 ± 0.13 (n = 2) | 4.50 ± 0.00 (n = 1) | 4.67 ± 0.47 (n = 3) | 4.50 ± 0.00 (n = 1) | 5.75 ± 0.20 (n = 3) | 8.38 ± 0.63 (n = 2) | - |
| Relative velocity | 1.00 ± 0.00 (n = 6) | 1.03 ± 0.08 (n = 2) | 1.17 ± 0.00 (n = 1) | 0.95 ± 0.07 (n = 3) | 0.98 ± 0.00 (n = 1) | 0.96 ± 0.02 (n = 3) | 0.97 ± 0.01 (n = 2) | - |

FIG. 9

SEQUENCE LISTING

```
<160> NUMBER OF SEQ ID NOS: 10

<210> SEQ ID NO 1
<211> LENGTH: 23
<212> TYPE: PRT
<213> ORGANISM: Artificial Sequence
<220> FEATURE:
<223> OTHER INFORMATION: Synthesized sequence or isolated from a natural
      source (e.g., marine cone snail of the genus Conus).
<220> FEATURE:
<221> NAME/KEY: MISC_FEATURE
<222> LOCATION: (1)..(1)
<223> OTHER INFORMATION: Xaa is any N-modified amino acid
<220> FEATURE:
<221> NAME/KEY: MISC_FEATURE
<222> LOCATION: (5)..(5)
<223> OTHER INFORMATION: Xaa is any acidic amino acid or an amide form
      thereof
<220> FEATURE:
<221> NAME/KEY: MISC_FEATURE
<222> LOCATION: (7)..(7)
<223> OTHER INFORMATION: Xaa is proline or hydroxy-proline
<220> FEATURE:
<221> NAME/KEY: MISC_FEATURE
<222> LOCATION: (8)..(8)
<223> OTHER INFORMATION: Xaa is any basic amino acid
<220> FEATURE:
<221> NAME/KEY: MISC_FEATURE
<222> LOCATION: (11)..(11)
<223> OTHER INFORMATION: Xaa is any non-aromatic hydroxyl amino acid
<220> FEATURE:
<221> NAME/KEY: MISC_FEATURE
<222> LOCATION: (12)..(12)
<223> OTHER INFORMATION: Xaa is any non-aromatic hydroxyl amino acid
<220> FEATURE:
<221> NAME/KEY: MISC_FEATURE
<222> LOCATION: (13)..(13)
```

```
<223> OTHER INFORMATION: Xaa is any basic amino acid
<220> FEATURE:
<221> NAME/KEY: MISC_FEATURE
<222> LOCATION: (14)..(14)
<223> OTHER INFORMATION: Xaa is any aromatic amino acid
<220> FEATURE:
<221> NAME/KEY: MISC_FEATURE
<222> LOCATION: (16)..(16)
<223> OTHER INFORMATION: Xaa is any basic amino acid
<220> FEATURE:
<221> NAME/KEY: MISC_FEATURE
<222> LOCATION: (17)..(17)
<223> OTHER INFORMATION: Xaa is any acidic amino acid or an amide form
      thereof
<220> FEATURE:
<221> NAME/KEY: MISC_FEATURE
<222> LOCATION: (18)..(18)
<223> OTHER INFORMATION: Xaa is any basic amino acid, or any
      sulfur-containing amino acid
<220> FEATURE:
<221> NAME/KEY: MISC_FEATURE
<222> LOCATION: (19)..(19)
<223> OTHER INFORMATION: Xaa is any hydrophobic or apolar amino acid, or
      any non-aromatic hydroxyl amino acid
<220> FEATURE:
<221> NAME/KEY: MISC_FEATURE
<222> LOCATION: (20)..(20)
<223> OTHER INFORMATION: Xaa is any basic amino acid
<220> FEATURE:
<221> NAME/KEY: MISC_FEATURE
<222> LOCATION: (22)..(22)
<223> OTHER INFORMATION: Where Xaa at position 23 is absent, this
      residue may be an amide form/amidated.
<220> FEATURE:
<221> NAME/KEY: MISC_FEATURE
<222> LOCATION: (23)..(23)
<223> OTHER INFORMATION: Xaa is absent or is any apolar amino acid or is
      an amide group.

<400> SEQUENCE: 1

Xaa Gly Cys Cys Xaa Gly Xaa Xaa Gly Cys Xaa Xaa Xaa Xaa Cys Xaa
1               5                   10                  15

Xaa Xaa Xaa Xaa Cys Cys Xaa
            20

<210> SEQ ID NO 2
<211> LENGTH: 22
<212> TYPE: PRT
<213> ORGANISM: Artificial Sequence
<220> FEATURE:
<223> OTHER INFORMATION: Synthesized sequence or isolated from a natural
      source (e.g., marine cone snail of the genus Conus).
<220> FEATURE:
<221> NAME/KEY: MISC_FEATURE
<222> LOCATION: (1)..(1)
<223> OTHER INFORMATION: Xaa stands for pyroglutamic acid
<220> FEATURE:
<221> NAME/KEY: DISULFID
<222> LOCATION: (3)..(15)
<220> FEATURE:
<221> NAME/KEY: DISULFID
<222> LOCATION: (4)..(21)
<220> FEATURE:
<221> NAME/KEY: DISULFID
<222> LOCATION: (10)..(22)

<400> SEQUENCE: 2

Xaa Gly Cys Cys Asn Gly Pro Lys Gly Cys Ser Ser Lys Trp Cys Arg
1               5                   10                  15

Asp His Ala Arg Cys Cys
            20

<210> SEQ ID NO 3
```

```
<211> LENGTH: 22
<212> TYPE: PRT
<213> ORGANISM: Artificial sequence
<220> FEATURE:
<223> OTHER INFORMATION: Synthesized sequence or isolated from a natural
      source.
<220> FEATURE:
<221> NAME/KEY: MISC_FEATURE
<222> LOCATION: (1)..(1)
<223> OTHER INFORMATION: Xaa stands for pyroglutamic acid

<400> SEQUENCE: 3

Xaa Gly Cys Cys Asn Gly Pro Lys Gly Cys Ser Ser Lys Trp Cys Arg
1               5                   10                  15

Asp Met Ala Arg Cys Cys
            20

<210> SEQ ID NO 4
<211> LENGTH: 22
<212> TYPE: PRT
<213> ORGANISM: Artificial Sequence
<220> FEATURE:
<223> OTHER INFORMATION: Synthesized sequence or isolated form a natural
      source.
<220> FEATURE:
<221> NAME/KEY: DISULFID
<222> LOCATION: (3)..(15)
<220> FEATURE:
<221> NAME/KEY: DISULFID
<222> LOCATION: (4)..(20)
<220> FEATURE:
<221> NAME/KEY: MISC_FEATURE
<222> LOCATION: (6)..(6)
<223> OTHER INFORMATION: Xaa stands for hydroxyproline
<220> FEATURE:
<221> NAME/KEY: MISC_FEATURE
<222> LOCATION: (7)..(7)
<223> OTHER INFORMATION: Xaa stands for hydroxyproline
<220> FEATURE:
<221> NAME/KEY: DISULFID
<222> LOCATION: (10)..(21)
<220> FEATURE:
<221> NAME/KEY: MISC_FEATURE
<222> LOCATION: (17)..(17)
<223> OTHER INFORMATION: Xaa stands for hydroxyproline
<220> FEATURE:
<221> NAME/KEY: MOD_RES
<222> LOCATION: (22)..(22)
<223> OTHER INFORMATION: C- TERMINAL AMIDATION

<400> SEQUENCE: 4

Arg Asp Cys Cys Thr Xaa Xaa Lys Lys Cys Lys Asp Arg Gln Cys Lys
1               5                   10                  15

Xaa Gln Arg Cys Cys Ala
            20

<210> SEQ ID NO 5
<211> LENGTH: 22
<212> TYPE: PRT
<213> ORGANISM: Artificial Sequence
<220> FEATURE:
<223> OTHER INFORMATION: Synthesized sequence or isolated from a natural
      source.
<220> FEATURE:
<221> NAME/KEY: DISULFID
<222> LOCATION: (3)..(15)
<220> FEATURE:
<221> NAME/KEY: DISULFID
<222> LOCATION: (4)..(20)
<220> FEATURE:
<221> NAME/KEY: MISC_FEATURE
<222> LOCATION: (6)..(6)
<223> OTHER INFORMATION: Xaa stands for hydroxyproline
```

```
<220> FEATURE:
<221> NAME/KEY: MISC_FEATURE
<222> LOCATION: (7)..(7)
<223> OTHER INFORMATION: Xaa stands for hydroxyproline
<220> FEATURE:
<221> NAME/KEY: DISULFID
<222> LOCATION: (10)..(21)
<220> FEATURE:
<221> NAME/KEY: MISC_FEATURE
<222> LOCATION: (17)..(17)
<223> OTHER INFORMATION: Xaa stands for hydroxyproline
<220> FEATURE:
<221> NAME/KEY: MOD_RES
<222> LOCATION: (22)..(22)
<223> OTHER INFORMATION: C-TERMINAL AMIDATION

<400> SEQUENCE: 5

Arg Asp Cys Cys Thr Xaa Xaa Arg Lys Cys Lys Asp Arg Arg Cys Lys
1               5                   10                  15

Xaa Met Lys Cys Cys Ala
            20

<210> SEQ ID NO 6
<211> LENGTH: 22
<212> TYPE: PRT
<213> ORGANISM: Artificial Sequence
<220> FEATURE:
<223> OTHER INFORMATION: Synthesized sequence or isolated from a natural
      source.
<220> FEATURE:
<221> NAME/KEY: DISULFID
<222> LOCATION: (3)..(15)
<220> FEATURE:
<221> NAME/KEY: DISULFID
<222> LOCATION: (4)..(20)
<220> FEATURE:
<221> NAME/KEY: MISC_FEATURE
<222> LOCATION: (6)..(6)
<223> OTHER INFORMATION: Xaa stands for hydroxyproline
<220> FEATURE:
<221> NAME/KEY: MISC_FEATURE
<222> LOCATION: (7)..(7)
<223> OTHER INFORMATION: Xaa stands for hydroxyproline
<220> FEATURE:
<221> NAME/KEY: DISULFID
<222> LOCATION: (10)..(21)
<220> FEATURE:
<221> NAME/KEY: MISC_FEATURE
<222> LOCATION: (17)..(17)
<223> OTHER INFORMATION: Xaa stands for hydroxyproline
<220> FEATURE:
<221> NAME/KEY: MOD_RES
<222> LOCATION: (22)..(22)
<223> OTHER INFORMATION: C-TERMINAL AMIDATION

<400> SEQUENCE: 6

Arg Asp Cys Cys Thr Xaa Xaa Lys Lys Cys Lys Asp Arg Arg Cys Lys
1               5                   10                  15

Xaa Leu Lys Cys Cys Ala
            20

<210> SEQ ID NO 7
<211> LENGTH: 22
<212> TYPE: PRT
<213> ORGANISM: Artificial Sequence
<220> FEATURE:
<223> OTHER INFORMATION: Synthesized sequence or isolated from a natural
      source.
<220> FEATURE:
<221> NAME/KEY: MISC_FEATURE
<222> LOCATION: (1)..(1)
<223> OTHER INFORMATION: Xaa stands for pyroglutamic acid
<220> FEATURE:
```

```
<221> NAME/KEY: DISULFID
<222> LOCATION: (4)..(16)
<220> FEATURE:
<221> NAME/KEY: DISULFID
<222> LOCATION: (5)..(21)
<220> FEATURE:
<221> NAME/KEY: MISC_FEATURE
<222> LOCATION: (8)..(8)
<223> OTHER INFORMATION: Xaa stands for hydroxyproline
<220> FEATURE:
<221> NAME/KEY: DISULFID
<222> LOCATION: (11)..(22)
<220> FEATURE:
<221> NAME/KEY: MISC_FEATURE
<222> LOCATION: (18)..(18)
<223> OTHER INFORMATION: Xaa stands for hydroxyproline
<220> FEATURE:
<221> NAME/KEY: MOD_RES
<222> LOCATION: (22)..(22)
<223> OTHER INFORMATION: C-TERMINAL AMIDATION

<400> SEQUENCE: 7

Xaa Arg Leu Cys Cys Gly Phe Xaa Lys Ser Cys Arg Ser Arg Gln Cys
1               5                   10                  15

Lys Xaa His Arg Cys Cys
            20

<210> SEQ ID NO 8
<211> LENGTH: 22
<212> TYPE: PRT
<213> ORGANISM: Artificial Sequence
<220> FEATURE:
<223> OTHER INFORMATION: Synthesized sequence or isolated from a natural
      source.
<220> FEATURE:
<221> NAME/KEY: MISC_FEATURE
<222> LOCATION: (1)..(1)
<223> OTHER INFORMATION: Xaa stands for pyroglutamic acid
<220> FEATURE:
<221> NAME/KEY: DISULFID
<222> LOCATION: (3)..(15)
<220> FEATURE:
<221> NAME/KEY: DISULFID
<222> LOCATION: (4)..(21)
<220> FEATURE:
<221> NAME/KEY: DISULFID
<222> LOCATION: (10)..(22)
<220> FEATURE:
<221> NAME/KEY: MOD_RES
<222> LOCATION: (22)..(22)
<223> OTHER INFORMATION: C-TERMINAL AMIDATION

<400> SEQUENCE: 8

Xaa Arg Cys Cys Asn Gly Arg Arg Gly Cys Ser Ser Arg Trp Cys Arg
1               5                   10                  15

Asp His Ser Arg Cys Cys
            20

<210> SEQ ID NO 9
<211> LENGTH: 20
<212> TYPE: PRT
<213> ORGANISM: Artificial Sequence
<220> FEATURE:
<223> OTHER INFORMATION: Synthesized sequence or isolated from a natural
      source.
<220> FEATURE:
<221> NAME/KEY: MISC_FEATURE
<222> LOCATION: (1)..(1)
<223> OTHER INFORMATION: Xaa stands for pyroglutamic acid
<220> FEATURE:
<221> NAME/KEY: DISULFID
<222> LOCATION: (3)..(13)
<220> FEATURE:
```

```
<221> NAME/KEY: DISULFID
<222> LOCATION: (4)..(19)
<220> FEATURE:
<221> NAME/KEY: DISULFID
<222> LOCATION: (8)..(20)
<220> FEATURE:
<221> NAME/KEY: MOD_RES
<222> LOCATION: (20)..(20)
<223> OTHER INFORMATION: C-TERMINAL AMIDATION

<400> SEQUENCE: 9

Xaa Asn Cys Cys Asn Gly Gly Cys Ser Ser Lys Trp Cys Arg Asp His
1               5                   10                  15

Ala Arg Cys Cys
            20

<210> SEQ ID NO 10
<211> LENGTH: 16
<212> TYPE: PRT
<213> ORGANISM: Artificial Sequence
<220> FEATURE:
<223> OTHER INFORMATION: Synthesized sequence or isolated from a natural
      source.
<220> FEATURE:
<221> NAME/KEY: DISULFID
<222> LOCATION: (1)..(9)
<220> FEATURE:
<221> NAME/KEY: DISULFID
<222> LOCATION: (2)..(15)
<220> FEATURE:
<221> NAME/KEY: DISULFID
<222> LOCATION: (4)..(16)
<220> FEATURE:
<221> NAME/KEY: MOD_RES
<222> LOCATION: (16)..(16)
<223> OTHER INFORMATION: C-TERMINAL AMIDATION

<400> SEQUENCE: 10

Cys Cys Asn Cys Ser Ser Lys Trp Cys Arg Asp His Ser Arg Cys Cys
1               5                   10                  15
```

MU-CONOTOXIN PEPTIDES AND USE THEREOF AS A LOCAL ANESTHETIC

The material in the ASCII text filed entitled 1727054_1.txt is hereby incorporated by reference in its entirety. The ASCII text file entitled 1727054_1.txt was created on 27 Jan. 2012 and the size 8 KB.

FIELD OF THE INVENTION

The present invention relates to novel mu-conotoxin peptides, biologically active fragments thereof, salts thereof, combinations thereof and for variants thereof. The invention also relates to their use in pharmaceutical composition for the treatment or prevention of pain, and their use in the preparation of an anesthetic.

BACKGROUND OF THE INVENTION

Venoms of the marine cone snail of the genus *Conus* are a rich and extremely diverse source of bioactive components. With more than 800 species of *Conus* available worldwide, cone snail venoms appear as one of the richest source of naturally occurring peptides exhibiting a wide array of biological activity. The conopeptides target numerous and various molecular entities including voltage-sensitive ion channels, ligand-gated ion channels and G-protein-coupled receptors, with high affinity and specificity (McIntosh et al., 1999; Olivera et al., 1985; Olivera et al., 1990). Among all existing conopeptides, only a minority has been extensively characterized from isolation, primary structure elucidation to precise molecular target identification. However, increasing attention has been brought to this research area as conopeptides provide new and important tools for dissecting the function of previously uncharacterised channels. This also allows opportunities for entirely new biomedical application with the use of new drugs acting on original physiological targets. This can be exemplified by the discovery and use of omega-conotoxins for differentiating particular calcium subtypes and the further use of one of them as a drug (Prialt®) in pain management (Kerr and Yoshikami, 1984; Olivera et al., 1984; Olivera et al., 1987).

The publication of the first representatives of the mu-conopeptide family occurred in 1983 with the characterization of the geographutoxins exhibiting a myotoxic activity (Sato et al., 1983). This was followed by the isolation and identification of several other mu-conopeptides since then. To date, a total of 9 mu-conopeptides have been so far characterized from 6 different cone snail species, including mainly piscivorous species and one molluscivorous species.

All these mu-conopeptides display a common primary structure demonstrated by the conserved position of the cysteine residues in the sequence. The disulfide bonding is between Cys1-Cys4, Cys2-Cys5 and Cys3-Cys6. This fold leads to a constrained tertiary structure that has been studied for several representatives of the mu-conopeptide family (Hill et al., 1996; Keizer et al., 2003; Nielsen et al., 2002; Ott et al., 1991; Wakamatsu et al., 1992). It has been demonstrated in numerous studies that the mu-conopeptides target more or less specifically various voltage-sensitive sodium channels (Becker et al., 1989; Bulaj et al., 2005; Cruz et al., 1985; Cruz et al., 1989; Fainzilber et al., 1995; French et al., 1996; Safo et al., 2000; Sato et al., 1991; West et al., 2002). Whatever the subtype of sodium channels targeted, the pharmacological effect always consists in a blockade of the channel conductance leading to an inhibition of the voltage-sensitive channel functionality.

Voltage-sensitive sodium channels (VSSCs) are transmembrane proteins fundamental for cell communication as they generate action potentials and enable its propagation in most vertebrate and invertebrate excitable cells. Presently 9 genes have been identified that code for mammalian VSSCs (Yu and Catterall, 2003). VSSCs are classified according to their sensitivity to tetrodotoxin (TTX), a toxin isolated in particular from the puffer fish. VSSCs blocked by TTX are known as TTX-sensitive, while the others are TTX-resistant channels. Each subtype of VSSC has a specialised function depending on its cellular and tissue localization.

VSSCs have a major role in the transmission of the action potential in muscles as well as in nerves, thus providing a key target in anaesthesia. Drugs such as lidocaine or procaine act through the inhibition of VSSCs present in sensory fibres (Scholz, 2002). However, inhibition does not occur equally in all fibres due to the presence of numerous VSSCs subtypes differently affected by the drugs. Among them, TTX-resistant VSSC subtypes have a predominant role in the transmission of pain and are currently not specifically targeted by any known drug. Furthermore, the short duration of time of lidocaine and procaine as well as the well-documented side-reactions or allergy in response to their application make them difficult to use as anaesthesics in specific cases. In this context, compounds allowing specific inhibition of TTX-resistant VSSCs would appear as a major achievement for pain control. As an example, the subtype Nav1.8 contributes to the initiation and maintenance of hyperalgesia. In early stages of neuropathic pain, the expression of Nav1.8 is reduced in the primary afferent neurones which are injured, while expression levels of Nav1.8 are maintained in adjacent neurones (Decosterd et al., 2002; Gold et al., 2003). However, two days following sciatic nerve injury there is a significant upregulation of Nav1.8 expression as well as a proportional increase in the TTX-resistant compound action potential, at a conduction velocity consistent with C fibres (Gold et al., 2003). This strongly supports an important role for Nav1.8 in neuropathic pain.

The VSSCs thus represent useful targets which inhibition or modulation allow anaesthesia, analgesia and pain control (Baker and Wood, 2001; Julius and Basbaum, 2001; Lee, 1976).

A large number of peptides as isolated mu-conotoxins are known from Patent Application WO 02/07678 (University of Utah Research Foundation and Cognetix, Inc.). However, this document provides an ambiguous and at times misleading description of the peptides so that it is difficult to rely on its disclosures. For the large part, most of the peptides described therein appear to have been only identified by molecular biology techniques, by the isolation and cloning of DNA coding for mu-conotoxin peptides, translating and determining the toxin sequence. Reliance only on such techniques can cause errors, since in nature the active amino acid residues may result from posttranslational modification of the encoded peptide, some which can not be directly discovered from the nucleotide sequence.

Recently, Patent Application WO 2004/0099238 (The University of Queensland) also disclosed novel mu-conotoxin peptides and derivatives thereof with their use as neuronally active sodium channel inhibitors (antagonists), in assays and probes and also in the treatment of conditions involving pain, cancer, epilepsy and cardiovascular diseases. This application also disclosed the use of these novel mu-conotoxin peptides in radio-ligand binding assays (RLB). It will be appreciated by a skilled person in the art that these results do not imply any biological activity of the mu-conotoxins but only a binding effect since it is known from the literature that some compounds (including a conotoxin) bind to their channel/receptor site without any biological activity (Fainzilber et al., 1994; Shichor et al., 1996). Moreover, potency indicated in these binding experiments would not be relevant to inhibitory potency in vitro or in vivo, thus leaving the reader ignorant of any potential biological inhibitory potency. Furthermore, the only inhibitory activity (IC50) on the expressed VSSCs channels mentioned are superior to 1 to 3 µM thus suggesting an even higher concentration for use in ex vivo or in vivo preparation.

Thus novel compounds with potent and long-lasting biological activity for application as anesthetics which have a good safety profile, only low or no side effects and the possibility to retreat, whenever necessary are still needed.

This object has been achieved by providing novel mu-conotoxin peptides, a biologically active fragment thereof, a salt thereof, a combination thereof and/or variants thereof. The peptides of the invention, which present a long duration of effects, can be useful in the preparation of an anesthetic and in the treatment of a pain.

SUMMARY OF THE INVENTION

The invention provides a mu-conotoxin peptide essentially comprising the amino acid sequence: Xaa1-Xaa2-Cys-Cys-Xaa3-Xaa4-Xaa5-Xaa6-Xaa7-Cys-Xaa8-Xaa9-Xaa10-Xaa11-Cys-Xaa12-Xaa13-Xaa14-Xaa15-Xaa16-Cys-Cys-Xaa17 [SEQ ID No 1], a biologically active fragment thereof, a combination thereof and/or variants thereof.

Furthermore, the invention provides an isolated and purified nucleic acid sequence comprising a nucleotide sequence encoding the amino sequence of the peptide of the invention.

The invention further provides a pharmaceutical composition comprising as an active substance a pharmaceutically effective amount of at least one peptide according to the invention and the use of said pharmaceutical composition, for the preparation of a medicament for the treatment or prevention of a disease associated with voltage-sensitive sodium channels.

The invention also provides the use of the pharmaceutical composition of the invention in the preparation of an anesthetic and its use in a method for providing musculoskeletal relaxation in a patient undergoing a surgical procedure requiring anesthesia.

Another aspect of the present invention relates to a method for the treatment or prevention of a pain.

DESCRIPTION OF THE FIGURES

FIG. 3 shows the effect of mu-conopeptide CnIIIA on the mouse hemidiaphragm contraction. (A) Effect of CnIIIA on the muscular contraction provoked by the direct stimulation of the mouse hemidiaphragm. Traces of contraction recorded in the absence and in the presence of 100 to 600 nM of CnIIIA. (B) Dose-response curve of the effect of CnIIIA on the contraction. For each concentration of CnIIIA, the maximal amplitude of the contraction is expressed on the basis of the control value. The theoretical curve was established from the equation indicated, the Hill number ($n_H$) being 1.78 and the CnIIIA concentration necessary for 50% inhibition of the contraction ($K_D$) being 150 nM. Mean value±SEM of n experiments.

FIG. 5 represents the effect of mu-conotoxin CnIIIA on the global action potential (GAP) of sciatic nerves isolated from mice. (A) GAP records in response to 0.05 ms stimulations at intensities that vary between 0.1 and 15 V in control conditions (no toxin added) and when nerves are treated with various concentrations of conotoxin CnIIIA (0.1 to 50 µM). (B) Amplitude of GAP in response to different intensities of 0.05 ms stimulations and to different concentrations of the CnIIIA toxin (left panel). (C) This table summarize the different parameters of the GAP recorded after 0.05 ms stimulations at various intensities (0.1 to 15 V). ([1]) Ratio between the maximum amplitude recorded after a 15 V stimulation with or without mu-conotoxin. ([2]) Intensity of stimulation corresponding to 50% of the maximal amplitude following a 15 V-stimulation. Mean value±SEM of n sciatic nerves.

FIG. 6 represents the effect of mu-conotoxin CnIIIA on the GAP of mice sciatic nerves, recorded in the presence of various concentrations (0.1 to 50 µM) of conotoxin. The maximal amplitudes of GAP, recorded at various concentrations (0.1 to 100 µM) of toxin, were expressed according to the control value. The theoretical curve was calculated according to the following equation: $A_{CnIIIA}/A_C = 1/[1([mu\text{-}conotoxin\ CnIIIA]/K_D)\eta_H]$. The Hill number ($n_H$) was 1.02 and the toxin concentration required to block 50% of the GAP ($K_D$) was 1.53 µM. Mean value±SEM of n sciatic nerves.

FIG. 8 shows the effect of mu-conotoxin CnIIIA on the global action potential (GAP) of olfactory nerves isolated from the European pike (*Esox lucius*). (A) GAP records in response to 8 ms stimulations at intensities that vary between 1 and 15 V in control conditions (no toxin added) and when nerves are treated with various concentrations of conotoxin CnIIIA (0.02 to 1 µM). (B) Amplitude of GAP in response to different intensities of 8 ms stimulations and to different concentrations of the CnIIIA toxin with different durations of contact (see the left panel). (C) This table summarize the different parameters of the GAP recorded after a 8 ms stimulation at various intensities (1 to 15 V). ([1])

Ratio between the maximum amplitude recorded after a 15 V stimulation with or without mu-conotoxin. ($^2$) Intensity of stimulation corresponding to 50% of the maximal amplitude following a 15 V-stimulation. Mean value±SEM of n olfactory nerves.

Figure 9:
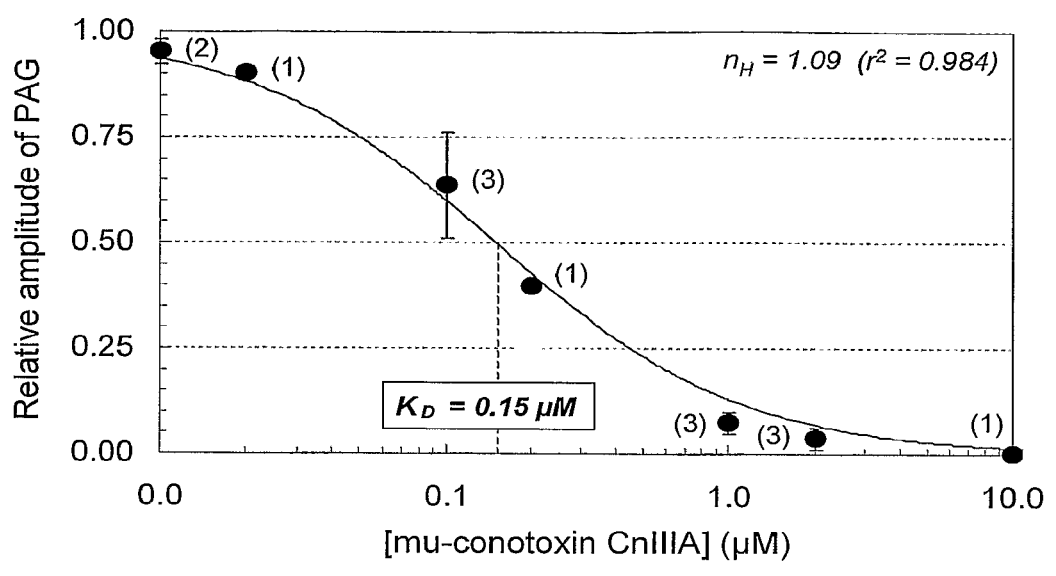

FIG. 9 shows the effect of mu-conotoxin CnIIIA on the GAP of olfactory nerves isolated from the European pike (*Esox lucius*) recorded in the presence of various concentrations (0.01 to 10 µM) of conotoxin, and expressed relatively to control values. The maximal amplitudes of GAP, recorded at various concentrations (0.1 to 10 µM) of toxin, were expressed according to the control value. The theoretical curve was calculated according to the following equation: $A_{CnIII}/A_C = 1/[1+([\text{mu-conotoxin CnIIIA}]/K_D)\eta_H]$. The Hill number ($n_H$) was 1.09 and the toxin concentration required to block 50% of the GAP ($K_D$) was 0.15 µM. Mean value±SEM of n olfactory nerves.

Figure 10:
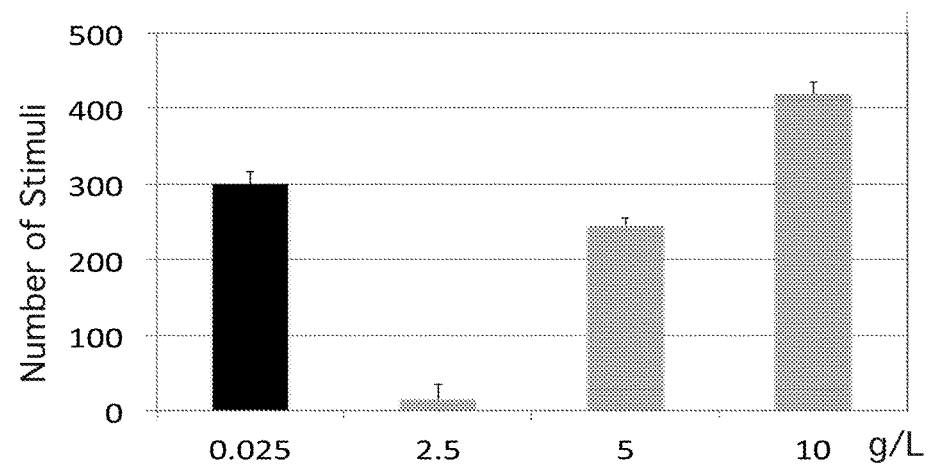

FIG. 10 shows in panel (A) a table summarizing the surface anaesthetic effect of µ-conotoxin CnIIIA and its comparison to that of lidocaine. The intensity of the anaesthetic effect is expressed as the total number of stimuli that fail to induce the oculo-palpebral reflex with each concentration tested. Data represent the mean values±S.E.M. of 6 different determinations. Panel (B) shows the same data from the table in panel (A), presented in bar chart form. Panel (C) shows a summary of published µ-conopeptide sequences in the literature, aligned relative to CnIIIA [SEQ ID No 2]. "Z" represents pyroglutamic acid residues. "O" represents hydroxyproline residues. The asterix ("*") denotes C-terminal amidation. The lines connecting cysteines underneath the alignment show disulfide pairings. The listed sequences have the following SEQ ID NO designations: CnIIIA=SEQ ID NO:2; GIIIA=SEQ ID NO:4; GIIIB=SEQ ID NO:5; GIIIC=SEQ ID NO:6; PIIIA=SEQ ID NO:7; SmIIIA=SEQ ID NO:8; SIIIA=SEQ ID NO:9; and KIIIA=SEQ ID NO:10.

Figure 11:
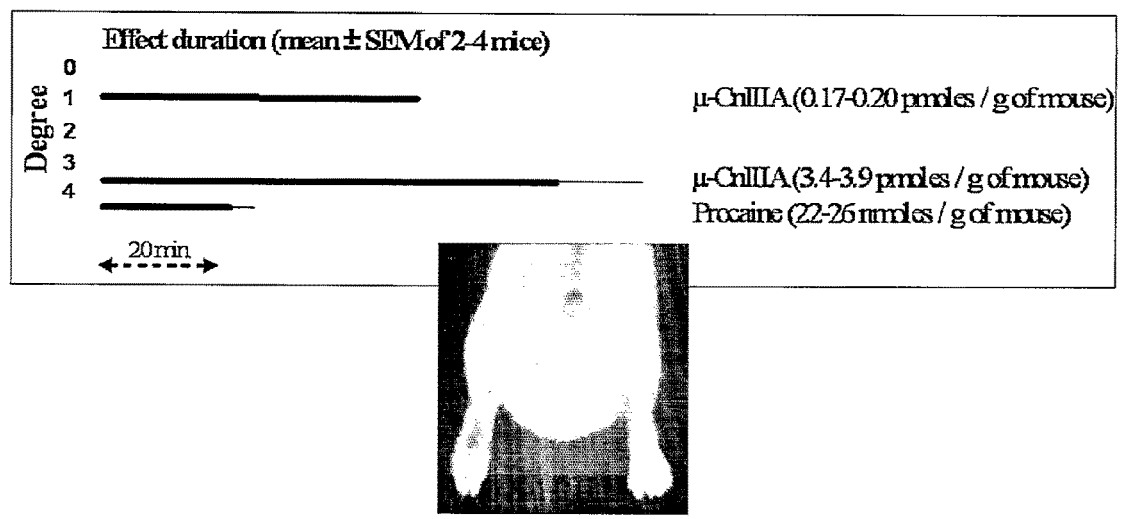

FIG. 11 shows the Digit Abduction Score (DAS) obtained in vivo on mice.

Figure 12:
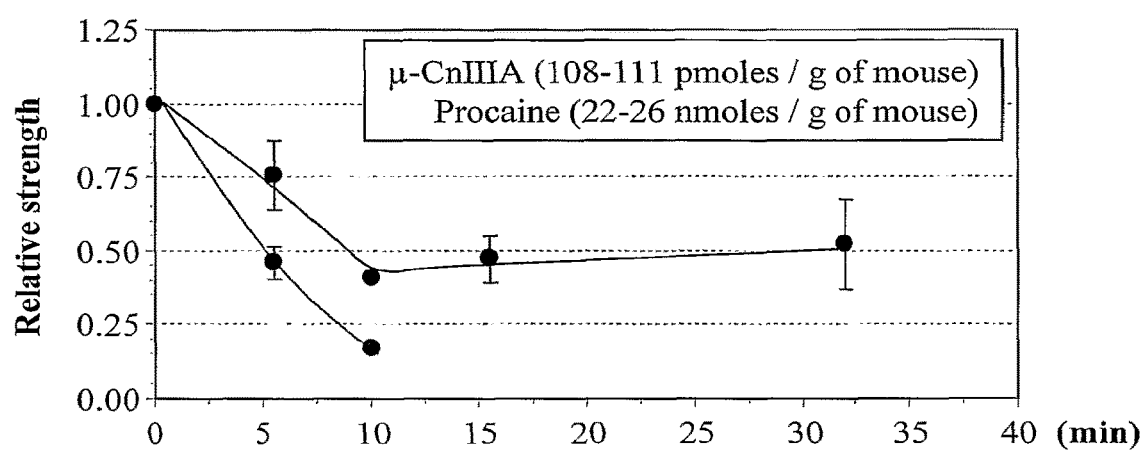

FIG. 12 shows the grip strength assessment obtained in vivo on mice

Figure 13:
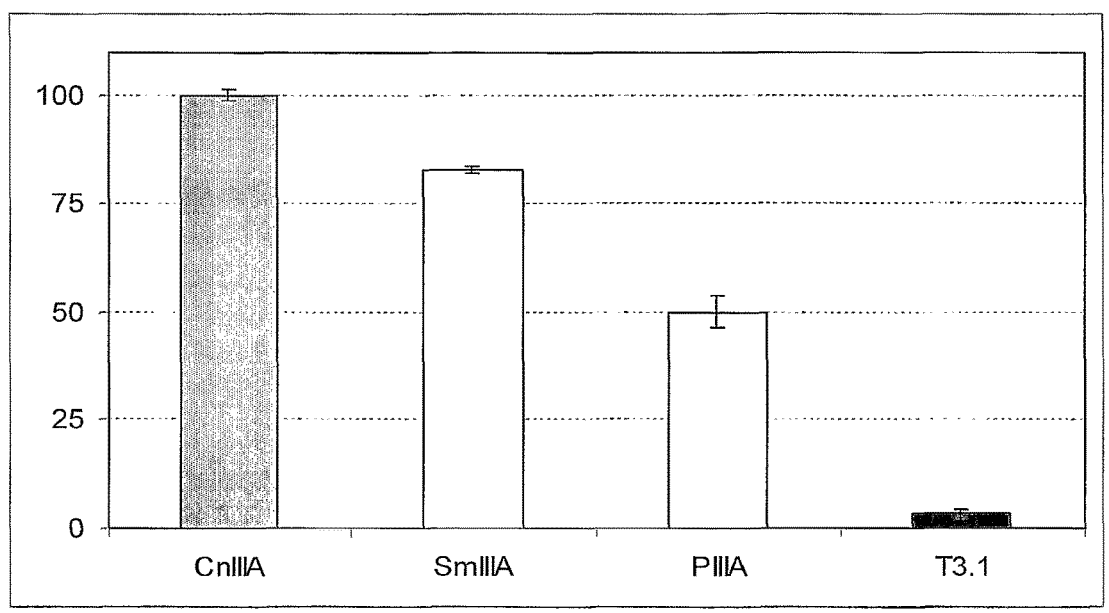
Figure 14:
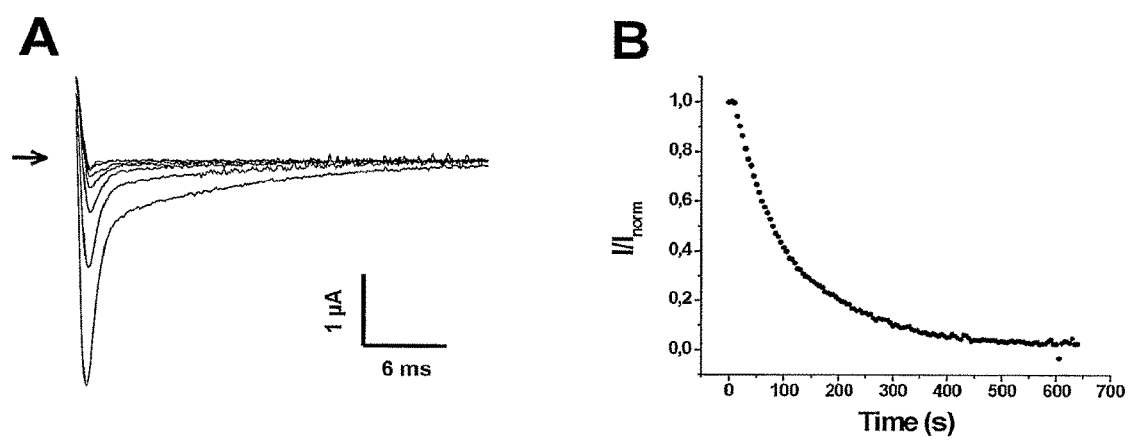

FIG. 13 shows the relative mean contraction inhibition of the muscle measured for each peptide (100 nM) by comparison to CnIIIA (100 nM) after 40 min. incubation. CnIIIA has been normalized to 100% for easy comparison. All peptides SmIIIA, PIIIA and T3.1 display a lower activity than CnIIIA.

FIG. 14 A) shows Nav1.4 current traces in function of time in the presence of 500 nM of CnIIIA. B) Nav1.4 current/Nav1.4 max. current is plotted over time with a CnIIIA concentration of 500 nM. The currents have been normalised to 1. The holding potential was −90 mV and test potential −10 mV.

FIG. 15 A) shows the sodium currents recorded in HEK cells as a control. B) in the presence of 50 nM CnIIIA and C) the sodium current inhibition by CnIIIA is shown in function of time. Note that the washing step after the steady-state level in not efficient in suppressing the blocking effect.

DETAILED DESCRIPTION OF THE INVENTION

As used herein,"a" or "an" means "at least one" or "one or more."

The terms "peptide", "protein", "polypeptide", "polypeptidic" and "peptidic", as used herein, are used interchangeably to designate a series of amino acid residues connected to the other by peptide bonds between the alpha-amino and carboxy groups of adjacent residues.

As used herein, the term "comprise" is generally used in the sense of include, that is to say permitting the presence of one or more features or components.

Conopeptides is an alternative term interchangeable with conotoxins and conotoxin peptides. The conotoxins are some of the most potent and diverse neurotoxins known, having an incredibly wide range of actions. Interestingly, a strong division exists not only between the mollusk eating and the fish eating species but also between species within a group or even individuals of the same species. The toxins from the fish hunting cone snails are also more bioactive upon the human system than the mollusc hunting cone snails, with deaths having occurred.

Three main classes of paralytic toxins have been the focus of intense investigation where all three interfere with neuronal communication but with different targets: alpha-conotoxins (α-conotoxins), binding to and inhibiting the nicotinic acetylcholine receptor; mu-conotoxins (μ-conotoxins), directly abolishing muscle action potential by binding to the postsynaptic sodium channels; and omega-conotoxins (ω-conotoxins), decimating the release of acetylcholine through the prevention of voltage activated entry of calcium into the nerve terminal.

Mu-conopeptides are isolated from the venoms of marine cone snails of the genus *Conus*. The primary structure of mu-conopeptides is organized with 15-30 amino acid folded by three disulfide bridges. These peptides target a variety of voltage-sensitive sodium channels that may be present either in muscles or in the nervous system. A number of the members of the mu-conopeptide class have been identified and their sequences published. GIIIA, GIIIB and GIIIC from *C. geographus* venom are potent blockers of skeletal muscle, but not neuronal VSSCs (Cruz et al., 1985). PIIIA from *C. purpurescens* was found to inhibit muscle and to a lesser extent neuronal TTX-Sensitive VSSCs (Shoe et al., 1998).

Unfortunately, these conotoxins are not particularly potent at neuronal VSSCs and are either selective for skeletal muscle VSSCs (GIIIA, GIIIB and GIIIC) or are not able to discriminate between skeletal muscle and neuronal VSSC subtypes (PIIIA). Furthermore, it has been demonstrated that these peptides lack three-dimensional (3D) structural stability and are prone to conformational exchange in solution (Nielsen et al., 2002). In the course of identifying and characterizing new conopeptides, Applicants have shown that a family of mu-conopeptides revealed extremely potent properties as a blocking agent of the mammalian neuromuscular junction as well as a powerful inhibitor of the action potential in motor neurons as well as in sensory neurons. This new mu-conotoxin peptide essentially comprises the amino acid sequence: Xaa1-Xaa2-Cys-Cys-Xaa3-Xaa4-Xaa5-Xaa6-Xaa7-Cys-Xaa8-Xaa9-Xaa10-Xaa11-Cys-Xaa12-Xaa13-Xaa14-Xaa15-Xaa16-Cys-Cys-Xaa17 [SEQ ID No 1], a biologically active fragment thereof, a salt thereof, a combination thereof and/or variants thereof, and wherein Cys represents a cystein.

Usually, Xaa1 is any N-modified acidic amino acid. Preferably, this modification is selected from the group comprising acetylation, formylation, myristoylation or pyrrolidone.

Formylation applies to methionine (N-formylmethionine). Acetylation applies to many residues including methionine (N-acetylmethionine), threonine (N-acetylthreonine,), serine (N-acetylserine), aspartic acid (N-acetylaspartate), glutamic acid (N-acetylglutamate), glycine, valine and alanine. Myristoylation applies to N-myristoylglycine Most preferably the acidic amino acid modified is pyroglutamate (pGlu or Z).

Xaa2 is preferably a glycine (Gly).

Xaa3 is any acidic amino acid or any of its amide form. Preferably, Xaa3 is an asparagine (Asn).

Xaa4 is usually a glycine (Gly).

Xaa5 is usually a proline or an hydroxyl-proline.

Xaa6 is any basic amino acid. Preferably Xaa6 is lysine (Lys).

Xaa7 is usually a glycine (Gly).

Xaa8 is any non-aromatic hydroxylamino acid. Preferably, Xaa8 is a serine (Ser).

Xaa9 is any non-aromatic hydroxylamino acid. Preferably, Xaa8 is a serine (Ser).

Xaa10 is any basic amino acid. Preferably, Xaa10 is a lysine (Lys).

Xaa11 is any aromatic amino acid. Preferably, Xaa11 is a tryptophan (Trp).

Xaa12 is any basic amino acid. Preferably, Xaa12 is an arginine (Arg).

Xaa13 is any acidic amino acid or any of its amide form. Preferably, Xaa13 is an aspartic acid (Asp).

Xaa14 is any basic amino acid or any sulfur-containing amino acid. Preferably, Xaa14 is a methionin (Met) or a histidine (His).

Xaa15 is any hydrophobic or apolar amino acid, or any non-aromatic hydroxyl amino acid. Preferably Xaa15 is an alanine (Ala).

Xaa16 is any basic amino acid. Preferably, Xaa16 is an arginine (Arg).

Xaa17 is apolar amino acid, or an amide group. Xaa17 may also be absent.

Optionally, in the mu-conotoxin described above, pairs of Cys residues may be replaced pairwise with isoteric lactam or ester-thioether replacements, such as Ser/(Glu or Asp), Lys/(Glu or Asp), Cys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues.

The present invention also relates to a mu-conotoxin wherein at least one amino acid consisting of amino acids Xaa3, Xaa4, Xaa5, Xaa6 and Xaa7, or any combination thereof, is absent (group 1).

Also envisioned is a mu-conotoxin wherein at least at least one amino acid consisting of amino acids Xaa8, Xaa9, Xaa10 and Xaa11, or any combination thereof, is absent (group 2).

Further completed is a mu-conotoxin peptide of the invention, wherein at least one amino acid consisting of amino acids Xaa12, Xaa13, Xaa14, Xaa15 and Xaa16, or any combination thereof, is absent (group 3).

Alternatively, the three above amino acids from group 1, 2 or 3, or combinations thereof, may be absent in the same mu-conotoxin peptide of the invention.

Exemplary hydrophobic amino acids with aliphatic R-groups include glycine (Gly), alanine (Ala), valine (Val), leucine (Leu) and isoleucine (Ile).

Exemplary amino acids with non-aromatic hydroxyl include serine (Ser) and threonine (Thr).

Exemplary sulfur-containing amino acids include cysteine (Cys) and methionine (Met).

Exemplary acidic amino acids and their amide forms include aspartic acid (Asp), asparagine (Asn), glutamic acid (Glu), glutamine (Gln) and pyroglutamic acid (pGlu).

Exemplary basic amino acids include arginine (Arg), lysine (Lys) and histidine (His).

Exemplary aromatic amino acids include phenylalanine (Phe), tyrosine (Tyr) and tryptophane (Trp).

Exemplary of imino acids include, for example, Proline (Pro) and Hydroxyproline (Hyp or Hpro or O).

The present invention also considers a "biologically active fragment" of the mu-conotoxin peptide, which refers to a sequence containing less amino acids in length than the sequence of the peptide. This sequence can be used as long as it exhibits essentially the same properties or biological activity as the native sequence from which it derives. Preferably this sequence contains less than 99%, preferably less than 90%, in particular less than 60% and more particularly less than 30% of amino acids in length than the respective sequence of the peptide of the invention.

Also envisioned is a salt of the mu-conotoxin peptide of the invention, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like.

Further encompassed in the present invention is a "prodrug" which is an entity representing an inactive form of an active mu-conotoxin peptide of the invention. In other words, the invention concerns a stable and soluble peptidic folding precursor (composition) which has the potential of producing a desired physiological effect on cells, but is initially inert (i.e. does not produce said effect), and only after undergoing some modifications becomes physiologically active and produces said physiological effect on cells i.e. becomes pharmaceutically active after biotransformation.

Biotransformation of the mu-conotoxin peptide may be carried out under physiological conditions (in vitro and in vivo) and is a result of a reaction with an enzyme, or a body fluid such as gastric acid, blood etc., thus undergoing an enzymatic oxidation, reduction, hydrolysis etc. or a chemical hydrolysis to convert into the active compound by acyl migration reaction.

The present invention also includes a variant of the mu-conotoxin peptide of the invention. The term "variant" refers to a peptide having an amino acid sequence that differ to some extent from a native sequence peptide, that is an amino acid sequence that vary from the native sequence by conservative amino acid substitutions, whereby one or more amino acids are substituted by another with same characteristics and conformational roles. The amino acid sequence variants possess substitutions, deletions, side-chain modifications and/or insertions at certain positions within the amino acid sequence of the native amino acid sequence. Conservative amino acid substitutions are herein defined as exchanges within one of the following five groups:

I. Small aliphatic, nonpolar or slightly polar residues: Ala, Ser, Thr, Pro, Gly II. Polar, positively charged residues: His, Arg, Lys III. Polar, negatively charged residues: and their amides: Asp, Asn, Glu, Gln IV. Large, aromatic residues: Phe, Tyr, Trp V. Large, aliphatic, nonpolar residues: Met, Leu, Ile, Val, Cys.

It is to be understood that some non-conventional amino acids may also be suitable replacements for the naturally occurring amino acids. For example Lys residues may be substituted by ornithine, homoarginine, nor-Lys, N-methyl- Lys, N,N-dimethyl-Lys and N,N, N-trimethyl-Lys. Lys residues can also be replaced with synthetic basic amino acids including, but not limited to, N-1-(2-pyrazolinyl)-Arg, 2-(4-piperinyl)-Gly, 2-(4-piperinyl)-Ala, 2-[3-(2S) pyrrolininyl]-Gly and 2-[3-(2S) pyrrolininyl]-Ala. Tyr residues may be substituted with 4-methoxy tyrosine (MeY), meta-Tyr, ortho-Tyr, nor-Tyr, 1251-Tyr, mono-halo-Tyr, di-halo-Tyr, O-sulpho-Tyr, O-phospho-Tyr, and nitro-Tyr.

Tyr residues may also be substituted with the 3-hydroxyl or 2-hydroxyl isomers (meta-Tyr or ortho-Tyr, respectively) and corresponding O-sulpho- and O-phospho derivatives. Tyr residues can also be replaced with synthetic hydroxyl containing amino acids including, but not limited to 4-hydroxymethyl-Phe, 4-hydroxyphenyl-Gly, 2,6-dimethyl-Tyr and 5-amino-Tyr. Aliphatic amino acids may be substituted by synthetic derivatives bearing non-natural aliphatic branched or linear side chains CnH2n+2 where n is a number from 1 up to and including 8. Examples of suitable conservative substitutions by non-conventional amino acids are given in WO2004/0099238 (see Table 1).

TABLE 1

| Non-conventional amino acid | Code | Non-conventional amino acid | Code |
|---|---|---|---|
| L-α-aminobutyric acid | Abu | L-α-methylhistidine | Mhis |
| α-amino-α-methylbutyrate | Mgabu | L-α-methylisoleucine | Mile |
| aminocyclopropane-carboxylate | Cpro | L-α-methylleucine | Mleu |
|  |  | L-α-methylmethionine | Mmet |
| aminoisobutyric acid | Aib | L-α-methylnorvaline | Mnva |
| aminonorbornyl-carboxylate | Norb | L-α-methylphenylalanine | Mphe |
|  |  | L-α-methylserine | Mser |
| cyclohexylalanine | Chexa | L-α-methyltryptophan | Mtrp |
| cyclopentylalanine | Cpen | L-α-methylvaline | Mval |
| D-alanine | DAla | N-(N-(2,2-diphenylethyl) carbamylmethylglycine | Nnbhm |
| D-arginine | DArg |  |  |
| D-asparagine | DAsn | 1-carboxy-1-(2,2-diphenyl-ethylamino)cyclopropane | Nmbc |
| D-aspartic acid | DAsp |  |  |
| D-cysteine | DCys | L-N-methylalanine | Nmala |
| D-glutamine | DGln | L-N-methylarginine | Nmarg |
| D-glutamic acid | DGlU | L-N-methylaspartic acid | Nmasp |
| D-histidine | DHis | L-N-methylcysteine | Nmcys |
| D-isoleucine | DIle | L-N-methylglutamine | Nmgln |
| D-leucine | DLeu | L-N-methylglutamic acid | Nmglu |
| D-lysine | DLys | L-N-methylhistidine | Nmhis |
| D-methionine | DMet | L-N-methylisolleucine | Nmile |
| D-ornithine | DOrn | L-N-methylleucine | Nmleu |
| D-phenylalanine | DPhe | L-N-methyllysine | Nmlys |
| D-proline | DPro | L-N-methylmethionine | Nmmet |
| D-serine | DSer | L-N-methylnorleucine | Nmnle |
| D-threonine | DThr | L-N-methylnorvaline | Nmnva |
| D-tryptophan | DTrp | L-N-methylornithine | Nmorn |
| D-tyrosine | DTyr | L-N-methylphenylalanine | Nmphe |
| D-valine | DVal | L-N-methylproline | Nmpro |
| D-α-methylalanine | DMala | L-N-methylserine | Nmser |
| D-α-methylarginine | DMarg | L-N-methylthreonine | Nmthr |
| D-α-methylasparagine | DMasn | L-N-methyltryptophan | Nmtrp |
| D-α-methylaspartate | DMasp | L-N-methyltyrosine | Nmtyr |
| D-α-methylcysteine | DMcys | L-N-methylvaline | Nmval |
| D-α-methylglutamine | DMgln | L-N-methylethylglycine | Nmetg |
| D-α-methylhistidine | DMhis | L-N-methyl-t-butylglycine | Nmtbug |
| D-α-methylisoleucine | DMile | L-norleucine | Nle |
| D-α-methylleucine | DMleu | L-norvaline | Nva |
| D-α-methyllysine | DMlys | α-methyl-aminoisobutyrate | Maib |
| D-α-methylmethionine | DMmet | α-methyl-γ-aminobutyrate | Mgabu |
| D-α-methylornithine | DMorn | α-methylcyclohexylalanine | Mchexa |
| D-α-methylphenylalanine | DMphe | α-methylcyclopentylalanine | Mcpen |
| D-α-methylproline | DMpro | α-methyl-α-napthylalanine | Manap |
| D-α-methylserine | DMser | α-methylpenicillamine | Mpen |
| D-α-methylthreonine | DMthr | N-(4-aminobutyl)glycine | Nglu |
| D-α-methyltryptophan | DMtrp | N-(2-aminoethyl)glycine | Naeg |
| D-α-methyltyrosine | DMty | N-(3-aminopropyl)glycine | Norn |
| D-α-methylvaline | DMval | N-amino-α-methylbutyrate | Nmaabu |
| D-N-methylalanine | DNmala | α-napthylalanine | Anap |
| D-N-methylarginine | DNmarg | N-benzylglycine | Nphe |
| D-N-methylasparagine | DNmasn | N-(2-carbamylethyl)glycine | Ngln |
| D-N-methylaspartate | DNmasp | N-(carbamylmethyl)glycine | Nasn |
| D-N-methylcysteine | DNmcys | N-(2-carboxyethyl)glycine | Nglu |
| D-N-methylglutanmine | DNmgln | N-(carboxymethyl)glycine | Nasp |
| (-carboxyglutamate | Gla | N-cyclobutylglycine | Ncbut |
| 4-hydroxyproline | Hyp | N-cyclodecylglycine | Ncdec |
| 5-hydroxylysine | Hlys | N-cylcododecylglycine | Ncdod |
| 2-aminobenzoyl (anthraniloyl) | Abz | N-cyclooctylglycine | Ncoct |
|  |  | N-cyclopropylglycine | Ncpro |
| Cyclohexylalanine | Cha | N-cycloundecylglycine | Ncund |
| Phenylglycine | Phg | N-(2,2-diphenylethyl)glycine | Nbhm |
| 4-phenyl-phenylalanine | Bib | N-(3,3-diphenylpropyl)glycine | Nbhe |
| L-pyroglutamic acid | pGlu | N-(1-hydroxyethyl)glycine | Nthr |
| L-Citrulline | Cit | N-(hydroxyethyl)glycine | Nser |

TABLE 1-continued

| Non-conventional amino acid | Code | Non-conventional amino acid | Code |
|---|---|---|---|
| L-1,2,3,4-tetrahydroiso-quinoline-3-carboxylic acid | Tic | N-(imidazolylethyl))glycine | Nhis |
| | | N-(3-indolylyethyl)glycine | Nhtrp |
| L-Pipecolic acid (homo proline) | Pip | N-methyl-γ-aminobutyrate | Nmgabu |
| | | D-N-methylmethionine | Dnmmet |
| L-homoleucine | Hle | N-methylcyclopentylalanine | Nmcpen |
| L-Lysine (dimethyl) | DMK | D-N-methylphenylalanine | Dnmphe |
| L-Napthylalanine | Nal | D-N-methylproline | Dnmpro |
| L-dimethyldopa or L-dimethoxyphenylalanine | DMD | D-N-methylthreonine | Dnmthr |
| | | N-(1-methylethyl)glycine | Nval |
| L-thiazolidine-4-carboxylic acid | THZ | N-methyla-napthylalanine | Nmanap |
| | | N-methylpenicillamine | Nmpen |
| L-homotyrosine | hTyr | N-(p-hydroxyphenyl)glycine | Nhtyr |
| L-3-pyridylalanine | PYA | N-(thiomethyl)glycine | Ncys |
| L-2-furylalanine | FLA | penicillamine | Pen |
| L-histidine(benzyloxymethyl) | HBO | L-α-methylalanine | Mala |
| L-histidine(3-methyl) | HME | L-α-methylasparagine | Masn |
| D-N-methylglutamate | Dnmglu | L-α-methyl-t-butylglycine | Mtbug |
| D-N-methylhistidine | Dnmhis | L-methylethylglycine | Metg |
| D-N-methylisoleucine | Dnmile | L-α-methylglutamate | Mglu |
| D-N-methylleucine | Dnmleu | L-α-methylhomophenylalanine | Mhphe |
| D-N-methyllysine | Dnmlys | N-(2-methylthioethyl)glycine | Nmet |
| N-methylcyclohexylalanine | Nmchexa | L-α-methyllysine | Mlys |
| D-N-methylornithine | Dnmorn | L-α-methylnorleucine | Mnle |
| N-methylglycine | Nala | L-α-methylornithine | Morn |
| N-methylaminoisobutyrate | Nmaib | L-α-methylproline | Mpro |
| N-(1-methylpropyl)glycine | Nile | L-α-methylthreonine | Mthr |
| N-(2-methylpropyl)glycine | Nleu | L-α-methyltyrosine | Mtyr |
| D-N-methyltryptophan | Dnmtrp | L-N-methylhomophenylalani | Nmhphe |
| D-N-methyltyrosine | Dnmtyr | N-(N-(3,3-diphenylpropyl) carbamylmethylglycine | Nnbhe |
| D-N-methylvaline | Dnmval | | |
| L-t-butylglycine | Tbug | O-methyl-L-serine | Omser |
| L-ethylglycine | Etg | O-methyl-L-homoserine | Omhser |
| L-homophenylalanine | Hphe | O-methyl-L-tyrosine | MeY |
| L-α-methylarginine | Marg | γ-aminobutyric acid | Gabu |
| L-α-methylaspartate | Masp | O-methyl-L-homotyrosine | Omhtyr |
| L-α-methylcysteine | Mcys | L-ꓱ-homolysine | BHK |
| L-α-methylglutamine | Mgln | L-ornithine | Orn |
| N-cycloheptylglycine | Nchep | N-cyclohexylglycine | Nchex |
| N-(3-guanidinopropyl)glycine | Narg | D-N-methylserine | DNmser |

Insertions encompass the addition of one or more naturally occurring or non conventional amino acid residues, although preferably not cysteine residues.

Deletion encompasses the deletion of one or more amino acid residues, although preferably not cysteine residues.

As stated above the present invention includes peptides in which one or more of the amino acids other than Cys has undergone side chain modifications.

Examples of side chain modifications contemplated by the present invention include modifications of amino groups such as by reductive alkylation by reaction with an aldehyde followed by reduction with NaBH4; amidation with methylacetimidate; acylation with acetic anhydride; carbamoylation of amino groups with cyanate; trinitrobenzylation of amino groups with 2,4,6 trinitrobenzenesulphonic acid (TNBS); acylation of amino groups with succinic anhydride and tetrahydrophthalic anhydride; and pyridoxylation of lysine with pyridoxal-5-phosphate followed by reduction with NaBH4; and N-acetylation.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Acidic amino acids may be substituted with tetrazolyl derivatives of glycine and alanine, as described in WO02/060923 (COGNETIX INC; Univ. Utah Res Found.).

The tyrosine residue may be altered, for example by methoxylation at the 4-position. Tyrosine may also be altered by nitration with tetranitromethane to form a 3-nitrolyrosine derivative.

Modification of the imidazole ring of a histidine residue may be accomplished by alkylation with iodoacetic acid derivatives or N-carbethoxylation with diethylpyrocarbonate.

Proline residue may be modified by, for example, hydroxylation in the 4-position.

Other variants contemplated by the present invention include a range of glycosylation variants. Altered glycosylation patterns may result from expression of recombinant molecules in different host cells. Ser, Thr and Hyp residues may be modified to contain an O-glycan, while Asn and Gln residues can be modified to form a N-glycan. In accordance with the present invention, the term "glycan" refers to an N-, S- or O-linked mono-, di-, tri-, poly- or oligosaccharide that can be attached to any hydroxy, amino or thiol group of natural of modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNac), D-fucose or D-arabinose. These saccharides may be structurally modified i.e., with one or more O-sulphate, O-phosphate, O-acetyl or acidic groups such as sialic acid, including combinations thereof. The glycan may also include similar polyhydroxyl groups, such as D-penicillamine 2,5 and halogenated derivatives thereof or polypropylene glycol derivatives. The glycosidic linkage is beta and 1-4 or 1-3, preferably 1-3.

The linkage between the glycan and the amino acid may be alpha or beta, preferably alpha and is 1-.

Furthermore, since an inherent problem with native peptides (in L-form) is the degradation by natural proteases, the peptide of the invention may be prepared in order to include D-forms and/or "retro-inverso isomers" of the peptide. Preferably, retro-inverso isomers of short parts, variants or combinations of the peptide of the invention are prepared.

Protecting the peptide from natural proteolysis should therefore increase the effectiveness of the specific heterobivalent or heteromultivalent compound. A higher biological activity is predicted for the retro-inverso containing peptide when compared to the non-retro-inverso containing analog owing to protection from degradation by native proteinases. Furthermore they have been shown to exhibit an increased stability and lower immunogenicity [Sela M. and Zisman E., (1997) Different roles of D-amino acids in immune phenomena-FASEB J. 11, 449].

Retro-inverso peptides are prepared for peptides of known sequence as described for example in Sela and Zisman, (1997).

By "retro-inverso isomer" is meant an isomer of a linear peptide in which the direction of the sequence is reversed and the chirality of each amino acid residue is inverted; thus, there can be no end-group complementarity.

The invention also includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as an active substance. Such mimetics, and methods of incorporating them into peptides, are well known in the art.

Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

The combination of the mu-conotoxin of the invention, or of particular biologically active fragments thereof, are envisioned and can be made to improve the potency, selectivity or stability of existing peptides of the invention.

Preferably, the mu-conotoxin peptide is selected from the group comprising pGlu-Gly-Cys-Cys-Asn-Gly-Pro-Lys-Gly-Cys-Ser-Ser-Lys-Trp-Cys-Arg-Asp-His-Ala-Arg-Cys-Cys [SEQ ID No 2] and pGlu-Gly-Cys-Cys-Asn-Gly-Pro-Lys-Gly-Cys-Ser-Ser-Lys-Trp-Cys-Arg-Asp-Met-Ala-Arg-Cys-Cys [SEQ ID No 3].

Usually, the C-terminus of these peptide are amidated.

It should also be understood that the terms mu-conotoxin peptide or mu-conotoxins are not limited to naturally occurring toxic peptides obtained from the genus Conus but rather simply indicates an initial source from which the peptides have been or can be derived. The mu-conotoxin peptide of the invention, as well as a fragment, combination and a variant thereof can be prepared by a variety of methods and techniques known in the art such as for example chemical synthesis or recombinant techniques as described in Maniatis et al. 1982, Molecular Cloning, A laboratory Manual, Cold Spring Harbor Laboratory and Amblard et al. 2005.

When recombinant techniques are employed to prepare mu-conotoxin peptides in accordance with the present invention, nucleic acid molecules or biologically active fragments thereof encoding the polypeptides are preferably used.

Therefore the present invention also relates to an isolated and purified nucleic acid sequence comprising a nucleotide sequence encoding the amino acid sequence as described above.

"An isolated and purified nucleic acid sequence" refers to the state in which the nucleic acid molecule encoding the mu-conotoxin peptide of the invention, or nucleic acid encoding such mu-conotoxin peptide will be, in accordance with the present invention. Nucleic acid will be free or substantially free of material with which it is naturally associated such as other polypeptides or nucleic acids with which it is found in its natural environment, or the environment in which it is prepared (e.g. cell culture) when such preparation is by recombinant nucleic acid technology practised in vitro or in vivo.

The term "nucleic acid" is intended to refer either to DNA or to RNA.

In case the nucleic acid is DNA, then DNA which can be used herein is any polydeoxynucleotide sequence, including, e.g. double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemically-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid.

DNA sequences that encode the mu-conotoxin peptide, or a biologically active fragment thereof, can be synthesized by standard chemical techniques, for example, the phosphotriester method or via automated synthesis methods and PCR methods.

The purified and isolated DNA sequence encoding the mu-conotoxin peptide according to the invention may also be produced by enzymatic techniques. Thus, restriction enzymes, which cleave nucleic acid molecules at predefined recognition sequences can be used to isolate nucleic acid sequences from larger nucleic acid molecules containing the nucleic acid sequence, such as DNA (or RNA) that codes for the mu-conotoxin peptide or for a fragment thereof.

Encompassed by the present invention is also a nucleic acid in the form of a polyribonucleotide (RNA), including, e.g., single-stranded RNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently cross-linked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

The isolated and purified nucleic acid sequence, DNA or RNA, also comprises an isolated and purified nucleic acid sequence having substantial sequence identity or homology to a nucleic acid sequence encoding the mu-conotoxin peptide of the invention. Preferably, the nucleic acid will have substantial sequence identity for example at least 50%, 55%, 60%, 65%, 70%, 75%, 80%, or 85% nucleic acid identity; more preferably 90% nucleic acid identity; and most preferably at least 95%, 96%, 97%, 98%, or 99% sequence identity.

Identity as known in the art and used herein, is a relationship between two or more amino acid sequences or two or more nucleic acid sequences, as determined by comparing the sequences. It also refers to the degree of sequence relatedness between amino acid or nucleic acid sequences, as the case may be, as determined by the match between strings of such sequences. Identity and similarity are well known terms to skilled artisans and they can be calculated by conventional methods (for example see Computational Molecular Biology, Lesk, A. M. ed., Oxford University Press, New York, 1988; Biocomputing: Informatics and Genome Projects, Smith, D. W. ed., Academic Press, New York, 1993; Computer Analysis of Sequence Data, Part I, Griffin, A. M. and Griffin, H. G. eds., Humana Press, New Jersey, 1994; Sequence Analysis in Molecular Biology, von Heinje, G. Academic Press, 1987; and Sequence Analysis Primer, Gribskov, M. and Devereux, J. eds. M. Stockton Press, New York, 1991, Carillo, H. and Lipman, D., SIAM J. Applied Math. 48:1073, 1988).

Methods which are designed to give the largest match between the sequences are generally preferred. Methods to determine identity and similarity are codified in publicly available computer programs including the GCG program package (Devereux J. et al., Nucleic Acids Research 12(1): 387, 1984); BLASTP, BLASTN, and FASTA (Atschul, S. F. et al. J. Molec. Biol. 215: 403-410, 1990). The BLAST X program is publicly available from NCBI and other sources (BLAST Manual, Altschul, S. et al. NCBI NLM NIH Bethesda, Md. 20894; Altschul, S. et al. J. Mol. Biol. 215: 403-410, 1990).

Also encompassed by the present invention is a nucleic acid sequence complementary to the isolated and purified nucleic acid sequence encoding mu-conotoxin peptide of the invention.

Also within the scope of the invention is a degenerated nucleic acid sequence having a sequence which differs from a nucleic acid sequence encoding the mu-conotoxin peptide of the invention, or a complementary sequence thereof, due to degeneracy in the genetic code. Such nucleic acid encodes functionally equivalent mu-conotoxin peptide but differs in sequence from the sequence due to degeneracy in the genetic code. This may result in silent mutations which do not affect the amino acid sequence. Any and all such nucleic acid variations are within the scope of the invention.

In addition, also considered is a nucleic acid sequence capable of hybridizing under stringent conditions, preferably high stringency conditions, to a nucleic acid sequence encoding the mu-conotoxin peptide of the invention, a nucleic acid sequence complementary thereof or a degenerated nucleic acid sequence thereof. Appropriate stringency conditions which promote DNA hybridization are known to those skilled in the art, or can be found in Current Protocols in Molecular Biology, John Wiley & Sons, N.Y. (1989), 6.3.1-6.3.6. For example, 6.0× sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

The present invention also includes an isolated and purified nucleic acid encoding a mu-conotoxin peptide of the invention comprising a nucleic acid sequence encoding a truncation or an analog of a mu-conotoxin peptide. The term “truncation” refers to a sequence encoding a peptide containing less amino acid than the native but exhibiting the same properties.

The invention also encompasses allelic variants of the disclosed isolated and purified nucleic sequence; that is, naturally-occurring alternative forms of the isolated and purified nucleic acid that also encode peptides that are identical, homologous or related to that encoded by the isolated and purified nucleic sequences. Alternatively, non-naturally occurring variants may be produced by mutagenesis techniques or by direct synthesis.

A biologically active fragment of the disclosed isolated and purified nucleic sequence is also considered and refers to a sequence containing less nucleotides in length than the nucleic acid sequence encoding the mu-conotoxin peptide, a nucleic acid sequence complementary thereof or a degenerated nucleic acid sequence thereof. This sequence can be used as long as it exhibits the same properties as the native sequence from which it derives. Preferably this sequence contains less than 90%, preferably less than 60%, in particular less than 30% amino acids in length than the respective isolated and purified nucleic sequence of the mu-conotoxin peptide.

Yet another concern of the present invention is to provide an expression vector comprising the isolated and purified nucleic acid sequence encoding the mu-conotoxin peptide. The choice of an expression vector depends directly, as it is well known in the art, on the functional properties desired, e.g., mu-conotoxin peptide expression and the host cell to be transformed or transfected.

Surprisingly, Applicants have shown that mu-conotoxin peptides as described herein demonstrated useful and potent biological activity for application as anaesthetics. These peptides clearly show a better activity than the currently used local anaesthetics such as procaine or lidocaine and a much longer duration time of activity. These mu-conotoxin can thus be applied to specific cases where long and efficient anaesthesia is required. They can also be used as alternatives in case of undesired side-reactions or allergy in response to classical anaesthetics such as procaine or lidocaine (Finucane B. T., 2005).

These mu-conotoxins also demonstrate better potency in biological activity by comparison to the data available in the scientific literature, in the patents cited above and the appended examples.

Accordingly, the present invention is also directed to a pharmaceutical composition comprising as an active substance a pharmaceutically effective amount of at least one mu-conotoxin peptide as described, optionally in combination with pharmaceutically acceptable carriers, diluents and/or adjuvants.

“A pharmaceutically effective amount” refers to a chemical material or compound which, when administered to a human or animal organism induces a detectable pharmacologic and/or physiologic effect.

The respective pharmaceutically effect amount can depend on the specific patient to be treated, on the disease to be treated and on the method of administration. Further, the pharmaceutically effective amount depends on the specific peptide used, especially if the peptide additionally contains a drug as described or not. The treatment usually comprises a multiple administration of the pharmaceutical composition, usually in intervals of several hours, days or weeks. The pharmaceutically effective amount of a dosage unit of the polypeptide usually is in the range of 0.001 ng to 100 µg per kg of body weight of the patient to be treated. Preferably in the range of 0.1 ng to 10 µg per kg of body weight.

Preferably, in addition to at least one mu-conotoxin peptide as described herein, the pharmaceutical composition may contain one or more pharmaceutically acceptable carriers, diluents and adjuvants.

Acceptable carriers, diluents and adjuvants which facilitates processing of the active compounds into preparation which can be used pharmaceutically are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

The form of administration of the pharmaceutical composition may be systemic or topical. For example, administration of such a composition may be various parenteral routes such as subcutaneous, intravenous, intradermal, intramuscular, intraperitoneal, intranasal, transdermal, buccal routes or via an implanted device, and may also be delivered by peristaltic means.

The present invention also contemplates an implant device comprising the mu-conotoxin or the pharmaceutical composition of the invention.

The pharmaceutical composition, as well as the anesthetic, comprising a mu-conotoxin peptide, as described herein, as an active agent may also be incorporated or impregnated into a bioabsorbable matrix, with the matrix being administered in the form of a suspension of matrix, a gel or a solid support. In addition the matrix may be comprised of a biopolymer.

Sustained-release preparations may be prepared. Suitable examples of sustained-release preparations include semi permeable matrices of solid hydrophobic polymers containing the mu-conotoxin peptide, which matrices are in the form of shaped articles, e.g. films, microspheres, implants or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma]ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished for example by filtration through sterile filtration membranes.

It is understood that the suitable dosage of a mu-conotoxin peptide of the present invention will be dependent upon the age, sex, health, and weight of the recipient, kind of concurrent treatment, if any and the nature of the effect desired.

The appropriate dosage form will depend on the disease, the peptide, and the mode of administration; possibilities include tablets, capsules, lozenges, dental pastes, suppositories, inhalants, solutions, ointments, creams and parenteral depots.

In the case of inhalants, then it is preferably in the form of a spray. A nasal formulation of the mu-conotoxin of the invention is made in order to provide, for example, efficient epithelial sodium channel inhibition. The amount injected via nasal spray is dependant of the subject characteristics, such as age and weight. Determination of an effective dose range is routine for those of skill in the art.

As an example of a specific formulation, the amount of mu-conotoxin in a daily nasal spray formulation with a volume between about 30 to about 300 μL, can deliver a daily dose of mu-conotoxin of between about 1 μg to about 10 μg. It will be appreciated that the daily spray volume can be administered in one, two, or more separate deliveries to achieve the desired total daily spray volume. It will further be appreciated that the spray volume and the amount of mu-conotoxin in the nasal formulation are each individually adjustable to achieve the desired daily dosage.

Since amino acid modifications of the amino acids of the mu-conotoxin peptide are also encompassed in the present invention, this may be useful for cross-linking the mu-conotoxin peptide of the invention to a water-insoluble matrix or the other macromolecular carriers, or to improve the solubility, adsorption, and permeability across the blood brain barrier. Such modifications are well known in the art and may alternatively eliminate or attenuate any possible undesirable side effect of the peptide and the like.

While a preferred pharmaceutical composition of the present invention comprises a mu-conotoxin peptide as an active agent, an alternative pharmaceutical composition may contain a isolated and purified nucleic acid sequence encoding the mu-conotoxin peptide, as described herein, as an active agent. This pharmaceutical composition may include either the sole isolated and purified DNA sequence, an expression vector comprising said isolated and purified DNA sequence or a host cell previously transfected or transformed with an expression vector described herein. In this latter example, host cell will preferably be isolated from the patient to be treated in order to avoid any antigenicity problem. These gene and cell therapy approaches are especially well suited for patients requiring repeated administration of the pharmaceutical composition, since the said purified and isolated DNA sequence, expression vector or host cell previously transfected or transformed with an expression vector can be incorporated into the patient's cell which will then produce the protein endogenously.

Usually, the pharmaceutical composition as described herein is used for the treatment or prevention of a pain. The pain to be treated or prevented will be selected, for example, from the group comprising migraine, acute pain, persistent pain, chronic pain, neuropathic pain or nociceptive pain.

Alternatively, the pharmaceutical composition as described herein is used for treating cystic fibrosis or oto-rhino-laryngological diseases.

Since the mu-conotoxin of the invention is a sodium channel inhibitor, it can be applied to the airway epithelium and nasal membrane for blocking the enhancement of sodium intake by the epithelial sodium channel. This has the effect of lowering the mucous viscosity and promote a better clearance of the external biological fluid, such as lung fluids and nasal fluids. In this respect, the mu-conotoxin inhibits at low concentrations the sodium channels present in membranes associated with cystic fibrosis disease and with inflammatory states where mucous production is above normal levels. Epithelial sodium channels modulate clearance of mucous lung or nasal fluids. Application of different concentrations of pharmaceutical composition comprising the mu-conotoxin of the invention in the micromalor and sub-micromolar range would induce better clearance of the accumulation of biological fluids in mucus. Mu-conotoxin thus has a therapeutic potential in treating oto-rhino-laryngological inflammatory states presenting abnormal fluid secretions in mucus. Mu-conotoxin application is also dedicated to the potential treatment of abnormal lung secretions arising in cystic fibrosis.

Also encompassed by the present invention is the use of the pharmaceutical composition of the invention, in the preparation of a medicament for the treatment or prevention of a disorder associated with voltage-sensitive sodium channels.

The mu-conotoxin peptide of the invention will generally be used in an amount to achieve the intended purpose. For use to treat or prevent a pain, the peptide or the pharmaceutical compositions thereof, is administered or applied in a therapeutically effective amount. A "therapeutically effective amount" is an amount effective to ameliorate or prevent the symptoms. Determination of a therapeutically effective amount is well within the capabilities of those skilled in the art, especially in light of the detailed disclosure provided herein.

For systemic administration, a therapeutically effective amount or dose can be estimated initially from in vitro assays. For example, a dose can be formulated in animal models to achieve a circulating concentration range that includes the IC50 as determined in cell culture. Such information can be used to more accurately determine useful doses in humans.

Initial doses can also be estimated from in vivo data, e.g. animal models, using techniques that are well known in the art. One ordinarily skill in the art could readily optimise administration to humans based on animal data and will, of course, depend on the subject being treated, on the subject's weight, the severity of the disorder, the manner of administration and the judgement of the prescribing physician.

Further encompassed by the present invention is the use of the pharmaceutical composition of the invention, in the preparation of an anesthetic.

The present disclosure also provides a method for providing musculoskeletal relaxation in a patient undergoing a surgical procedure requiring anesthesia which comprises administering to a patient in need thereof a pharmaceutically effective amount of at least one mu-conotoxin peptide of the invention or a pharmaceutically acceptable salt thereof.

"Administered" or "administering", as it applies in the present invention means "giving" or "contacting" and refers to contact of a pharmaceutical, therapeutic, or anesthetic composition to the subject, preferably a human.

Usually, in the method described above, the at least one mu-conotoxin peptide is administered as a local anesthetic. Preferably, the at least one mu-conotoxin peptide is used in, for example, ophthalmology, in the treatment of dystonia, in otolaryngology, in the treatment of anal fissures, in dermatology, in traumatology, in cosmetic surgery, in the treatment of fibromyalgia and chronic myofascial pain as well as in the treatment of all pains.

Preferably, the at least one mu-conotoxin peptide is administered as an ocular anesthetic.

Also encompassed in the present invention is a method for local anesthesia, said method comprising administering a pharmaceutically effective amount of at least one mu-conotoxin peptide of the invention or a pharmaceutically acceptable salt thereof. Preferably, said pharmaceutically effective amount of at least one mu-conotoxin peptide of the invention or the pharmaceutical composition provides a long and duration of effect as disclosed in the Examples.

Preferably, the long duration of effect is about 30 min to 48 hours depending on the subject to be treated and/or the concentration of mu-conotoxin of the invention used. However, in any case said duration is longer than any duration described until now for classical anesthetics such as lidocaine of procaine. Preferably, the duration is 30 min to 12 hours.

Further encompassed by the present invention is an anesthetic comprising the pharmaceutical composition or the mu-conotoxin peptide of described in the present disclosure.

Preferably said anesthetic is suitable for subcutaneous, intravenous, intradermal, intramuscular, intraperitoneal, intranasal, transdermal, buccal routes or an implanted device.

Usually, the anesthetic is in the form of tablets, capsules, lozenges, dental pastes, suppositories, inhalants, solutions, ointments, creams and parenteral depots. Preferably, the inhalant is a spray.

EXAMPLES

Example 1

Material and Methods

Materials

Specimens of *Conus consors* were collected in chesterfield Island (New Calcdonia) and immediately frozen at −80° C. The venom was obtained from freshly dissected venom duct apparatus, and extracted with 0.08% trifluoroacetic acid (TFA) in water. Extracts obtained from several venom ducts were centrifuged to remove insoluble particles. Supernatants from all extractions were combined, lyophilised, weighed, and stored at −80° C. until required for use.

Chromatography

Fractionation of the crude lyophilised venom was performed using a Thermo Separation Product (TSP) high pressure liquid chromatography system equipped with a TSP-150 UV detector. Elution buffers used for reverse-phase chromatography were the following: buffer A, H2O/0.1% TFA; buffer B, H2O/CH3 CN 40/60 0.1% TFA. Semi-preparative runs on the crude venom were performed with a C18 Vydac 218TP510 column using the following gradient. The program was 0-8% B/5 min., 8-80% B/70 min., 80-100% B/10 min., followed by 100% B/10 min. (flow rate, 2 ml/min). Further purification steps using an analytical C18 Vydac 218TP54 column was carried out with gradient such as 0-10% B/5 min., 10-20% B/10 min., 20-40% B/40 min. Fractions were detected at 220 nm.

Amino Acid Composition and Edman Sequencing

Peptide samples were hydrolyzed by addition of 200 ml of 6 M HCl at the bottom of the vial which was evacuated, sealed and heated at 120° C. for 16 h. The hydrolysates were analysed on an automatic analyser (Applied Biosystems, model 130A) equipped with an on-line derivatiser (model 420A) for the conversion of the free amino acids into their phenylthiocarbamoyl derivatives. Sequencing trials were performed by Edman's degradation on an automatic Applied Biosystems 477A microsequencer. Before sequencing, the homogeneous peptide was reduced by dithiothreitol in 6 M guanidine hydrochloride, 0.5 M Tris/HCl, 2 mM ethylene-diamine tetraacetic acid (EDTA) (pH 7.5) for 1 h and then treated with 4-vinylpyridine (1.5 µM) at room temperature for 3 h. The peptide derivative was purified by reverse-phase HPLC using a $C_{18}$ Vydac column (4.6 mm×25 cm, 5 µm particle size).

Mass Spectrometry

Molecular mass measurements were performed on a QTOF I instrument (Micromass/Waters, USA) equipped with an electrospray ion source. Sample analysis was carried out in positive mode using a carrier infusion solvent of H2O/CH3 CN/HCOOH (49.9/49.9/0.2). Single MS experiments with the TOF-MS configuration was used for simple molecular mass determination. Tandem mass spectrometry was carried out for structural investigations. In this configuration, parent mass was first selected using the quadrupole, and the collision induced dissociation was performed by manually adjusting the collision energy. In this case, the native sample was previously reduced using 100 mM dithiothreitol (DTT) in an ammonium bicarbonate buffer (pH 7.8) at 56° C. for 3 h. The reduced peptide was then desalted using a ZipTip (Millipore, USA) according to the manufacturer protocol. The multiply-charged spectra obtained were transformed into singly-charged data with the aid of the software MassLynx (Micromass/Waters, USA) using the MaxEnt3 option. Manual and semi-automatic data treatment was then operated for sequence characterisation.

Peptide Synthesis

Solid-phase synthesis was performed on a custom-modified 433A peptide synthesizer from Applied Biosystems, using in situ neutralization/2-(1H-benzotriazol-1-yl)-1,1,1,3,3-tetramethyluronium hexa fluoro-phosphate (HBTU) activation protocols for stepwise Boc chemistry chain elongation. After chain assembly was completed, the peptide was deprotected and cleaved from the resin by treatment with anhydrous HF for 1 hr at 0° C. with 5% p-cresol as a scavenger. After cleavage, the peptide was precipitated with ice-cold diethylether, dissolved in aqueous acetonitrile and lyophilized. The peptide was purified by RP-HPLC with a Vydac C18 column by using a linear gradient of buffer B (acetonitile/10% $H_2O$/0.1% trifluoroacetic acid) in buffer A ($H_2O$/0.1% trifluoroacetic acid) and UV detection at 214 nm. Samples were analyzed by electrospray mass spectrometry with a Platform II instrument (Micromass, Manchester, England).

For the oxidative folding of the peptide, the material (about 0.5 to 1 mg/mL) was dissolved in 0.5M GuHCl, 100 mM Tris, pH 7.8 containing 0.5 mM reduced and 0.1 mM oxidized glutathione. After gentle stirring overnight at room temperature, the protein solution was purified by RP-HPLC as described above. The overall yield of the folding step was of approximately 35%.

Frog and Mouse Neuromuscular Preparations

The cutaneous pectoris muscle and associated nerve were removed from double pithed male frogs (*Rana esculenta*) weighing 20-25 g. and pinned to the base of a 2 ml tissue bath superfused with a standard solution containing (in mM): NaCl, 115.0; KCl, 2.0; $CaCl_2$, 1.8 and HEPES buffer, 5.0 (pH 7.25). In some experiments, excitation-contraction was uncoupled by treating the cutaneous pectoris neuromuscular preparations with 2 M formamide. Left and right hemidiaphragm muscles with their associated phrenic nerves were isolated from Swiss-Webster mice (20-25 g) that were killed by dislocation of the cervical vertebrae followed by immediate exsanguination. The two hemidiaphragms were separated and each was mounted in a Rhodorsil (Rhone-Poulenc, St. Fons, France)-lined organ bath (2 ml volume) superfused with a physiological solution (mammalian Krebs-Ringer's solution) of the following composition (in mM): NaCl, 154.0; KCl, 5.0; $CaCl_2$, 2; $MgCl_2$, 1.0; HEPES buffer, 5.0; glucose, 11.0. The solution, gassed with pure $O_2$, had a pH of 7.4.

Mouse Sciatic Nerve Preparation

Both sciatic nerves (left and right) were dissected from mice killed by dislocation of the cervical vertebrae. The nerves were rinsed with oxygenated mammalian Krebs-Ringer's solution at room temperature for 30 min prior use.

Pike Olfactory Nerve Preparation

Left and right olfactory nerves were removed from decapitated pikes (*Esox lucius*). Each nerve was rinsed with an oxygenated pike Ringer's solution (82.5 mM NaCl, 2.5 mM KCl, 1 mM $CaCl_2$, 1 mM $Na_2HPO_4$ buffer, 5 mM HEPES, 1 mM $MgCl_2$, adjusted at pH 7.3 with NaOH), at room temperature for a 30-min period prior use.

Mechanical Recordings on Mouse Neuromuscular Preparations

In this type of experiments, one end of the mouse hemidiaphragm muscle is pined to the tissue bath and the other end (tendon) is attached to an isometric transducer (FT03, Grass Instruments). Contractions are evoked by stimulation of the motor nerve, via a suction electrode, with current pulses of 0.15 ms duration at a 0.1 Hz frequency. The resting tension of each preparation is adjusted so that maximal contractile response is obtained in normal conditions, with direct stimulation of the muscle or indirect stimulation via the motor nerve. Tension signals recorded from the transducer are amplified, collected and digitized with the aid of a computer equipped with a digital interface (DT-2821, Data Translation). Experiments are carried out at room temperature.

Electrophysiology Recordings on Frog and Mouse Neuromuscular Preparations

The motor nerve of isolated neuromuscular preparations was stimulated via a suction microelectrode, adapted to the diameter of the nerve, with pulses of 0.05-0.1 msec duration and supramaximal voltage (typically 3-8 V). These pulses were generated by a S-44 stimulator (Grass Instruments, West Warwick, U.S.A.) linked to a stimulus isolation unit.

Membrane potentials and synaptic potentials were recorded from endplate regions at room temperature (22-24° C.) with intracellular microelectrodes filled with 3 M KCl (8-12Ω resistance) using conventional techniques and an Axoclamp-2A system (Axon Instruments, Foster city, CA, U.S.A.). Recordings were made continuously from the same endplate before and throughout application of the conotoxin tested. Electrical signals after amplification were displayed on a digital oscilloscope and simultaneously recorded on video tape with the aid of a modified digital audio processor (Sony PCM 701 ES) and a video cassette recorder (Sony SLC9F). Data were collected and digitized with the aid of a computer equipped with an analogue and digital I/O interface board (DT2821, Data Translation Marlboro, U.S.A.) at a sampling rate of 25 kHz. Computerized data acquisition and analysis was performed with a program kindly provided by Dr. John Dempster (University of Strathclyde, Scotland). Endplate potentials (EPPs) and miniature endplate potentials (MEPPs) were analyzed individually for amplitude and time course. For each condition studied, 3-6 individual experiments were performed and the results were averaged to give the presented mean±standard error of the mean (S.E.M.). Statistical testing was performed by using student's test with P<0.05 being taken to indicate significance.

Electrophysiology Recordings on Mouse and Pike Nerves

The sciatic nerve from mice or the pike olfactory nerve was mounted onto two pairs of platinum wires (internal diameter 0.5 mm) connected to a Plexiglas chamber. For stimulation, the first pair of electrodes was connected to a stimulator (S-88, Grass Instruments) that was delivering rectangular pulses of current at various amplitude and time. For the recording of the global action potential (GAP), the second pair of electrodes was connected to a home made differential amplifier at high gain. An additional platinum wire was connecting both pairs of electrodes to the ground. In response to the electric stimulation, the nervous activity was collected, digitised and recorded on a computer equipped with an analogue and digital converter with the aid of the software program Axon Pclamp version 6.0 (Axon instruments). All experiments were performed at room temperature. During recording, the nerve was maintained in a humid chamber without any close contact to any solution to avoid any short circuit. Between each recording, the nerve was placed at 4° C., in a small container filled with either Ringer's or test solution.

In Vivo Experiments on Rabbit Eyes

The local anaesthetic activity of CnIIIA on superficial nerve terminal endings was determined on the rabbit cornea in vivo. For this, adult male Chilean rabbits with coloured eyes weighing 1.5-2 kg were used. The test solution was instilled into the conjunctival sac of one of the eyes and left there for 2 min. Stimuli were applied to the cornea by pressure from a nylon hair stimulator at a frequency of about 2 Hz until the oculo-palpebral reflex was evoked. Each period of stimulation consisted of 100 stimuli, or less if the oculo-palpebral reflex was evoked. An interval of at least 5 min separated two stimulation periods. The intensity of the anaesthetic action was expressed as the total number of stimuli that could be applied to the cornea from the administration of a test or anaesthetic solution until the reappearance of the oculo-palpebral reflex. This method allowed also determining the duration of the effect. Lidocaine HCl (Sigma-Aldrich) was used in saline solution and its pH value was adjusted to 6.9±0.01 with 1 N NaOH.

Example 2

Results

Isolation, Purification and Characterization of a Novel Mu-Conopeptide

Figure 1:
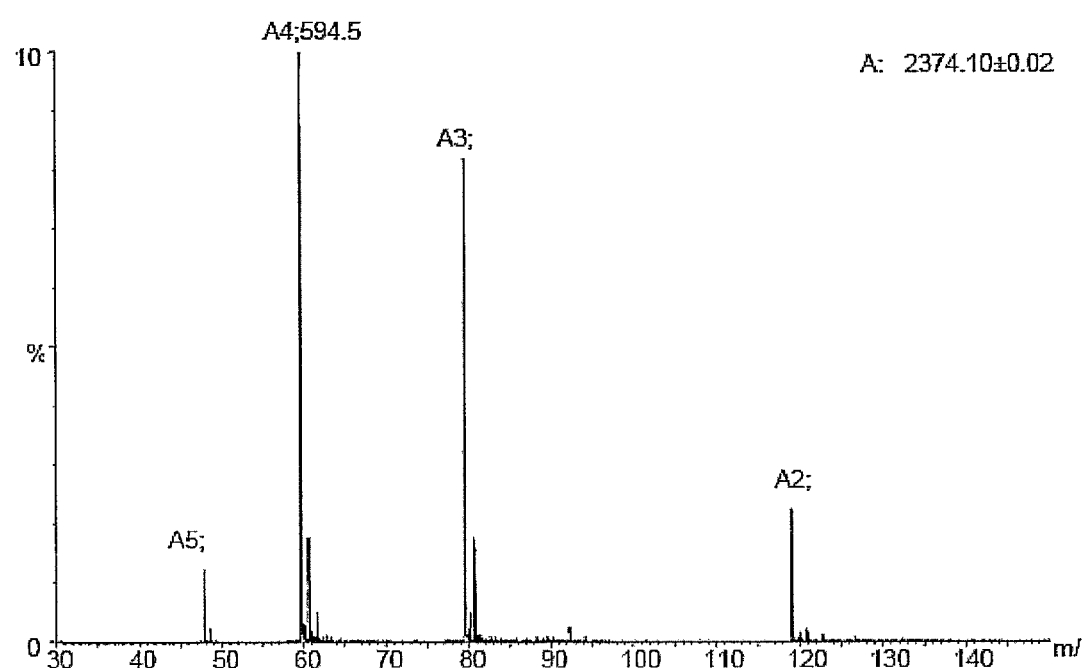
FIG. 1 represents an electrospray ionization mass spectrum of the native mu-conopeptide CnIIIA. Mass measurement was carried out on a QTOF I mass spectrometer in positive ion mode and TOF-MS configuration. The mass indicated is the measured monoisotopic molecular mass. A potassium adduct of CnIIIA can be noticed.

The dried venom was dissolved in 0.08% TFA in water and loaded in batches of 10 mg on a semipreparative C18 Vydac column. A fraction eluting, at approximately 20 min in the chromatogram, was further purified at an analytical scale. This fraction revealed a potent preliminary activity on frog neuromuscular junction. Application of this fraction into this ex vivo preparation induced a block of the muscle contraction provoked by stimulating the motor nerve. This fraction was eventually purified to homogeneity as demonstrated by the UV chromatogram and the ESI-MS mass spectrum (FIG. 1). The fraction was then subjected to Edman degradation several times, but did not give any result. Amino acid analysis of the fraction led to the identification of several different amino acids (results not shown), thus indicating that the fraction was of peptidic nature but with a probable blocked N-terminus. To further characterize the compound, the fraction was reduced using DTT and the sample was desalted prior analysis. Tandem mass spectrometry was then performed on the desalted sample. Selection of the 4× charged species at m/z 596 and manual adjustment of the collision energy allowed proper and homogeneous fragmentation of the peptide. Manual interpretation of the data led to the assignment of a peptide sequence bearing 22 amino acids. The sequence shared homology with previously published mu-conopeptides and was thus named CnIIIA (table 4).

Chemical Synthesis of CnIIIA

Figure 2:
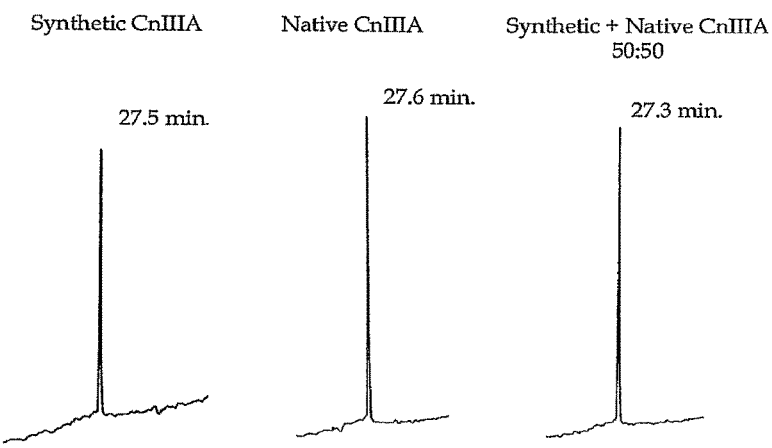
FIG. 2 depicts the control of the identity of the synthetic and native mu-conopeptide CnIIIA. (A) Co-elution experiments by reverse-phase HPLC of synthetic, native and 50:50 mixture of both peptides. (B) MS/MS of the reduced synthetic CnIIIA (up) along with the reduced native CnIIIA (down), showing identical fragmentation behaviour.
Figure 2:
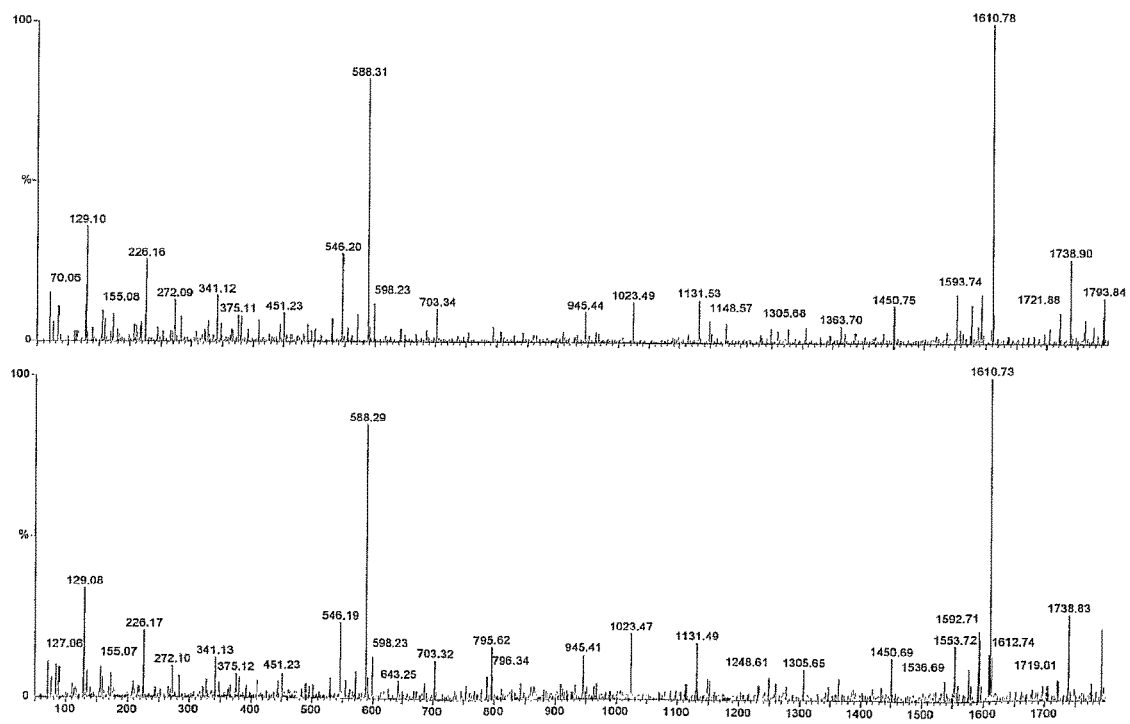

The peptide was assembled as described above (see Peptide synthesis). The synthetic peptide was purified to homogeneity by reverse-phase HPLC using a gradient of ACN in acidified water. Peptide purity and integrity were controlled by ESI-MS. Several conditions were explored for the oxidative refolding of the linear peptide. The peptide was dissolved in a Tris buffer (100 mM) at pH 7.8 with guanidinium chloride (0.5M), and left either under air oxidation at 4° C. or in mixtures containing various ratio of reduced/oxidized gluthation. The final refolding experiment was carried out using Tris 100 mM, guanidinium chloride 0.5M and reduced/oxidized gluthation 0.5 mM/0.1 mM. This mixture was left under stirring overnight at room temperature. It was then acidified using acetic acid, and concentrated using a C18 SepPak cartridge following manufacturer protocols. The final folded peptide was purified by reverse-phase chromatography at a semi-preparative scale. It appeared homogeneous and led to an approximate yield of 35% starting from the linear entity. The purity of the synthetic compound was assessed by HPLC and ESI-MS analysis. The authenticity of the synthetic peptide with the natural form was confirmed by HPLC co-elution and MS/MS analysis (FIG. 2). Synthetic CnIIIA was thus used for the different biological assays.

Effect on the Mouse Hemidiaphragm Contraction

The activity of CnIIIA was assessed on the muscle contraction induced by direct mouse hemidiaphragm stimulation (FIG. 3). In each condition (absence or presence of various CnIIIA concentrations), the contraction was recorded in response to stimulations of 250 µs and of variable intensity. This allowed to determine the supramaximal stimulation intensity, i.e. the intensity necessary to obtain maximal contraction amplitude. For each CnIIIA concentration, muscle contraction recordings were carried out 2 h. after peptide application to the preparation in order to saturate toxin receptor sites. As shown in FIG. 3A, the amplitude of the contraction decreases in the presence of 100 and 300 nM CnIIIA up to a complete inhibition with 600 nM CnIIIA. By comparison, a concentration of at least 2 µM mu-conotoxin GIIIA or GIIIB is necessary for complete block of the same preparation in identical conditions. The CnIIIA thus appears at least 4 times more potent than existing mu-conotoxins tested in this ex vivo model. The dose-response curve of the effect of CnIIIA reveals that the CnIIIA concentration producing half maximal inhibition of the mouse hemidiaphragm contraction is 150 nM (FIG. 3B).

Similar results were obtained when muscle contraction was induced by the stimulation of the motor nerve (results not shown).

Effect on Synaptic Responses at the Mouse Neuromuscular Junction

In order to assess the CnIIIA selectivity of action between muscle and nerve tissues, intracellular recordings of synaptic responses were performed at the mouse hemidiaphragm neuromuscular junction, after application of 600 nM CnIIIA. Firstly, results showed that the membrane resting potential of fibres was unchanged compared to controls. This indicates that the inhibition of muscle contraction does not result from a depolarising effect of CnIIIA. Secondly, miniature endplate potentials (MEPPs) could be detected in the presence of CnIIIA, thus demonstrating that the sensitivity of the nicotinic acetylcholine receptors was not altered at doses producing complete blockade of the muscle contraction. Finally, in the presence of 600 nM of CnIIIA, the nerve stimulation was able to give rise to phasic synaptic responses. Hence, endplate potentials (EPPs), similar to controls, could be recorded. This indicates that the nerve conduction was not altered at this conotoxin concentration. Moreover, extracellular current recordings allowed the detection of a presynaptic current, which reflects the presence of the presynaptic nerve action potential in motor nerve endings. A postsynaptic current was also observed, due to the opening of cationic synaptic channels in the muscle membrane.

Figure 4:
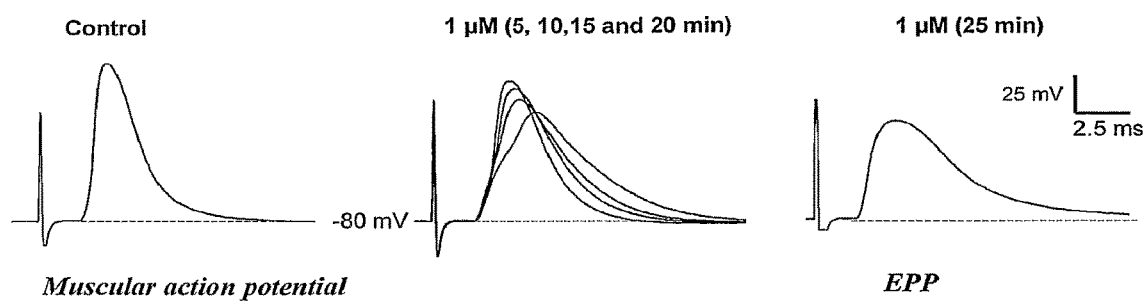
FIG. 4 shows the effects of mu-conopeptide CnIIIA on the action potential and the synaptic responses recorded at the frog *Cutaneous pectoris* muscle preparation. (A) Effects of CnIIIA on the muscular action potential recorded at the frog *Cutaneous pectoris* muscle: action potential traces and EPP recorded in response to motor nerve stimulation, before and at different time points after application of 1 µM of CnIIIA to the bathing solution. A progressive block of the muscular action potential can be noticed. (B) Effects of CnIIIA on the synaptic responses recorded at the frog *Cutaneous pectoris* muscle: average traces of MEPPs recorded in the absence and presence of 1 and 2 µM of CnIIIA.
Figure 4:
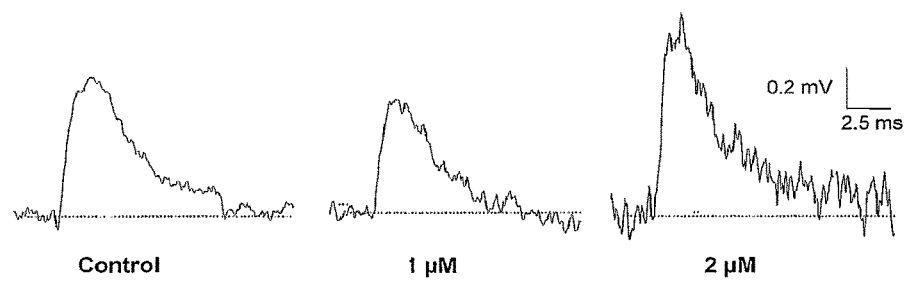

Effects on the Muscle Action Potential and Synaptic Responses at Frog Neuromuscular Preparations The effects of CnIIIA were studied on the frog cutaneous pectoris nerve-muscle preparation (FIG. 4). In this preparation, uncoupling the excitation-contraction is easily achieved by formamide treatment, thus allowing intracellular recordings of muscle action potentials induced by nerve stimulation without movement. Results showed that in the presence of 2 μM CnIIIA, the membrane resting potential of fibres is similar to controls. Application of 1 μM CnIIIA to the preparation, for 5-20 min. caused a decrease in amplitude and an increase in duration of action potentials evoked by motor nerve stimulation. After 25 min, the muscle action potential was completely abolished whereas EPPs could still be recorded. Similar effects, although occurring faster, were observed in the presence of higher concentrations of CnIIIA (2 μM). It should be noted that the latency time between nerve stimulation and muscle response was not significantly affected by the conotoxin. CnIIIA applications (1 and 2 μM) also did not alter the amplitude and the frequency of MEPPs compared to controls. These results strongly suggest that the inhibition of the skeletal muscle contraction, produced by the conotoxin CnIIIA, results from a preferential blockade of the muscle action potential, which is thus more sensitive to the conotoxin than the nerve action potential.

Effect on the Global Action Potential (GAP) of the Mouse Sciatic Motor Nerve

Applicants optimized the duration and intensity of the stimulation to get a GAP that represents the activity of all the fibres constituting the nerve. For a given duration of stimulation (0.10, 0.05 or 0.01 ms), the GAP amplitude increased with increasing intensity of the stimulation applied (0.1 to 15 V), as a consequence of an enhancement in the number of fibres recruited. In response to a stimulation intensity equal or superior than 7 V, the GAP amplitude reached a maximum value which remained constant whatever the stimulation duration (0.05 or 0.10 ms). This means that all the fibres of the nerve responded to the stimulation. In contrast, a 0.01 ms-stimulation was not sufficient to recruit all the fibres, as the maximum amplitude of the GAP was only 92% of that recorded after a stimulation of 0.05 or 0.10 ms. To study the effect of CnIIIA on the GAP, the duration of the stimulation was thus set to 0.05 ms and the intensity applied increased from 0.1 to 15 V. However, in order to attest that our experimental conditions were optimal for any concentration of CnIIIA studied, stimulations of 0.10 ms at various intensities were also applied. At concentrations ranging from 0.1 to 50 μM, CnIIIA was found to decrease the GAP amplitude which reached an almost zero value when the nerve was treated during 30 to 60 min with 50 μM CnIIIA (FIG. 5A, B). In addition, the stimulation intensity necessary to reach 50% of the GAP maximum amplitude increased with increasing conotoxin concentration (FIG. 5C). Finally, CnIIIA did not significantly modify the propagation velocity of GAP.

Altogether, these results show conclusively that the mu-conotoxin CnIIIA acts on mice sciatic nerves by decreasing the response of individual fibres without altering significantly their membrane excitability.

The dose-response curve of the effect of CnIIIA on the mouse sciatic nerve revealed that a concentration of 1.53 μM of conotoxin reduced by 50% the maximum GAP amplitude of the sciatic nerves (FIG. 6). These data show that the motor nerve response is ten times less sensitive to CnIIIA than the muscle contraction response. These results also indicate that the mu-conotoxin is about 1000 times more potent than classical anaesthetics such as lidocaine on the mouse sciatic nerve. Millimolar concentrations of lidocaine are indeed necessary to obtain similar inhibitory effect on mouse sciatic nerve.

Figure 7:
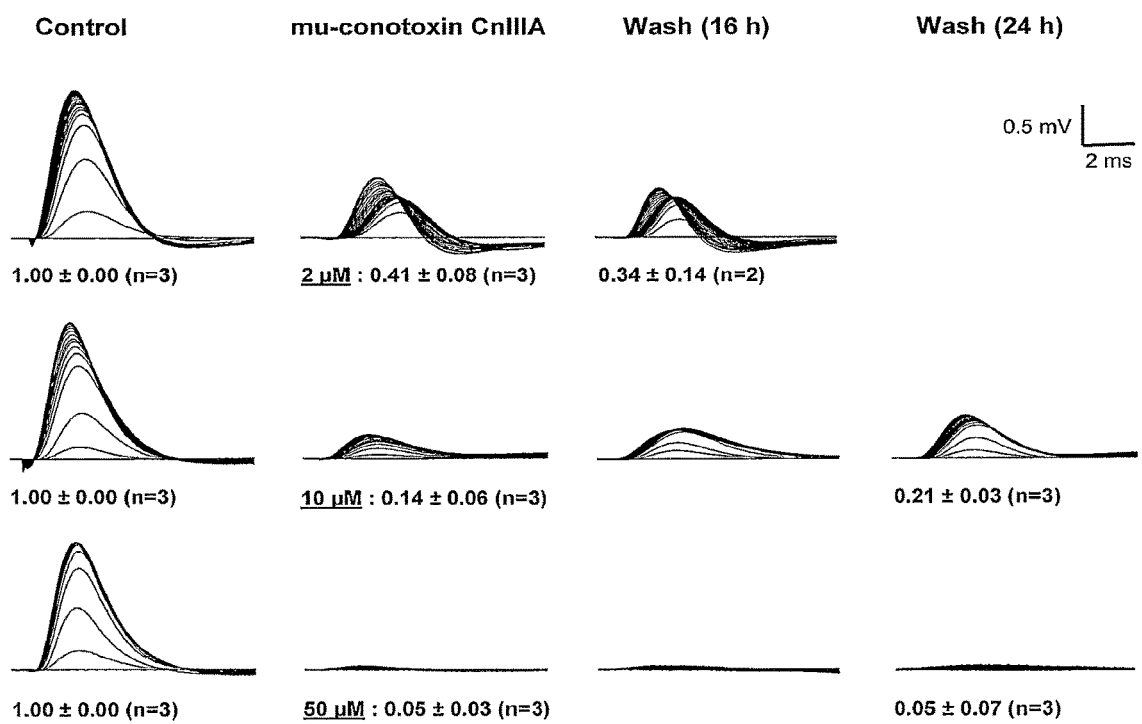
FIG. 7 depicts the study of the reversibility of the mu-conotoxin CnIIIA effect on the GAP of sciatic nerves isolated from mice. The GAP were recorded following a 0.05 ms stimulation at various intensities (0.1 to 15 V) in control conditions versus nerves treated with 2, 10 or 50 µM of CnIIIA toxin or washed during 16 h or 24 h in fresh mammalian Ringer's solution. Mean values±SEM of n sciatic nerves.

The reversibility of the effect of CnIIIA was evaluated by recording the GAP of sciatic nerves firstly in the presence of various concentrations of conotoxin (2, 10 and 50 μM), and secondly at various times (from 2 to 24 h) after the immersion of nerves in a mammalian Ringer's solution devoid of CnIIIA. Even after a 24 h washing, only a slight increase in the GAP amplitude was observed (FIG. 7). To test whether the absence of reversibility could be due to a spontaneous decrease of the GAP amplitude as a function of time ("run-down" phenomenon), the GAP of sciatic nerves was recorded at various times (from 2 to 66 h) after bathing the nerves only in a mammalian Krebs-Ringer's solution. Under these conditions, no significant modification of the GAP amplitude was observed.

Altogether, these data strongly suggest that mu-conotoxin CnIIIA is firmly associated to a receptor site on mouse sciatic nerves, i.e. the dissociation of the complex conotoxin/receptor occurs rather slowly.

Effect on the Global Action Potential (GAP) of the Olfactory Nerves of Pike

The sensory olfactory nerve of the European pike (Esox lucius) contains approximately five millions of relatively homogenous (95%) unmyelinated axons with an average diameter of 0.20 μm. This nerve has a high density of axonal membrane packing, and is therefore an exceptional model for biophysical, electrophysiological and pharmacological investigations. The optimal conditions (intensity and duration of stimulations) for recording the GAP of all the fibres constituting this sensory nerve were previously reported (Benoit et al., 2000). All the fibres of the olfactory nerve were recruited for an intensity and duration of stimulation of 8-9 V and 7-8 ins, respectively. Under such conditions, the maximum amplitude of the response was 2.77±0.15 mV (n=37), and propagated at a velocity of 12±0.5 cm/s (n=37) which is 60 times slower than in the sciatic nerve composed of myelinated axons. Therefore, the effect of CnIIIA was studied on the GAP of the pike olfactory nerve using stimulations of 8 ms duration and of 1-15 V intensities. A decrease of the GAP amplitude was observed when the olfactory nerves were treated with increasing concentrations of conotoxin, and no GAP could be recorded with 10 μM of conotoxin applied for 30-60 min (FIG. 8A, B). In addition, the intensity of stimulation corresponding to 50% of maximum GAP amplitude (i.e. recorded at 15 V) increased with increasing concentrations of conotoxin. Finally, CnIIIA did not significantly modify the propagation velocity of the GAP (FIG. 8C).

Altogether, these results show conclusively that CnIIIA acts on the pike olfactory nerve by decreasing the response of individual fibres without altering significantly their membrane excitability.

The dose-response curve of the effect of CnIIIA on the pike olfactory nerve revealed that a concentration of 0.15 μM of conotoxin reduced by 50% the maximum GAP amplitude of olfactory nerves (FIG. 9). These data show that the response of unmyelinated axons constituting the olfactory sensory nerve is as sensitive to CnIIIA as the mouse muscle (see FIG. 3B) and is ten times more sensitive to the mu-conotoxin than the response of myelinated axons constituting the sciatic motor nerve (see FIG. 6).

The reversibility of the effect of CnIIIA was evaluated by recording the GAP of pike olfactory nerves firstly in the presence of various concentrations of conotoxin (1, 2 and 10 μM), and secondly at various times (from 12 to 24 h) after the immersion of nerves in a pike Ringer's solution devoid of CnIIIA. Even after a 24 h washing, no increase in the GAP amplitude could be detected. To test whether the absence of reversibility was due to a spontaneous decrease of the GAP amplitude in function of time ("run-down" phenomenon), the GAP of olfactory nerves was recorded after bathing the nerves only in a pike Ringer's solution, under various experimental conditions: (i) at room temperature in the experimental chamber for a period of 30-60 min (n=10), (ii) at room temperature in the pike Ringer's solution for less than 3 h (n=14), and (iii) at 4° C. in the pike Ringer's solution for 48 h (n=66) and for 72 h (n=46). Whatever the experimental conditions were, no significant modification of the GAP amplitude was observed.

Altogether, these data strongly suggest that mu-conotoxin CnIIIA is firmly associated to a receptor site on the pike olfactory nerve, i.e. the dissociation of the complex conotoxin/receptor occurs rather slowly.

Surface Anaesthetic Effect of CnIIIA in Rabbit Eyes, and Comparison to that of Lidocaine Results obtained on the rabbit cornea indicate that the duration of anaesthetic action of lidocaine at concentrations of 2.5, 5.0 and 10 g/l was 5.3, 14.2 and 22.3 min, respectively. CnIIIA was not only more active than lidocaine on equimolar basis, but also its duration of action lasted longer, as shown in FIG. 10. The intensity of the anaesthetic action of CnIIIA, expressed as the sum of the number of stimuli applied to the corneal surface until the reappearance of the blinking reflex, was also more important than for lidocaine. Interestingly, the corneal reflex recovered without detectable damage of the mucous surface after CnIIIA.

In Vitro Experiments on Sodium Current Recorded from HEK Cells by Patch-Clamp

Patch-clamp current recordings were performed in HEK 293 cells stably expressing the rat skeletal muscle Na channel α subunit (μl, $Na_v1.4$) (Yamagishi et al., 1997). These cells display robust Na currents (>2 nA), are sensitive to saxitoxin (STX) and derivatives (Velez et al., 2001), and have a small size (diameter <20 μm), allowing an appropriate control of the holding potential.

Whole-cell patch-clamp recordings (Hamill et al., 1981) were performed at room temperature (20-22° C.) on HEK 293 cells stably expressing $Na_v1.4$ channels. Patch pipettes made from borosilicate glass and pulled on a P-97 puller (Sutter Instrument Company, Novato, Calif.) had a 1.5-3.0 MΩ tip resistances when filled with internal physiological solution. Membrane currents were recorded using an Axopatch 200-B patch-clamp amplifier (Axon Instruments, Union City, Calif.). Peak sodium currents were elicited by 10-ms depolarizing pulses from a holding voltage of −100 to −10 mV. A P/4 protocol was used to subtract linear capacitative and leak currents. Membrane currents were filtered with an integrated 8-pole low-pass Bessel filter at 10 kHz. The filtered signals were digitized by a 12 bit A/D converter (Digidata 1200B, Axon Instruments) and stored using pCLAMP software (Axon Instruments). Recordings were analyzed using Origin 7 software (OriginLab Corp., Northampton, Mass.).

The cells were continuously perfused at 1 ml $min^{-1}$ with a control external solution containing (in mM): 70 NaCl, 70 tetraethylammonium chlorhidrate, 5 KCl, 3 $CaCl_2$, 1 $MgCl_2$, 10 mM glucose, 10 HEPES (pH 7.4). The patch pipette contained (in mM) 140 CsF, 5 NaCl, 1 $MgCl_2$, 10 EGTA, 10 HEPES buffer (pH 7.2). Na currents were recorded under control conditions and after perfusion with different concentrations of μ-conotoxin CnIIIA (μ-CnIIIA) or with saxitoxin diacetate (STX) (Sigma-Aldrich Chemical Corp).

Figure 15:
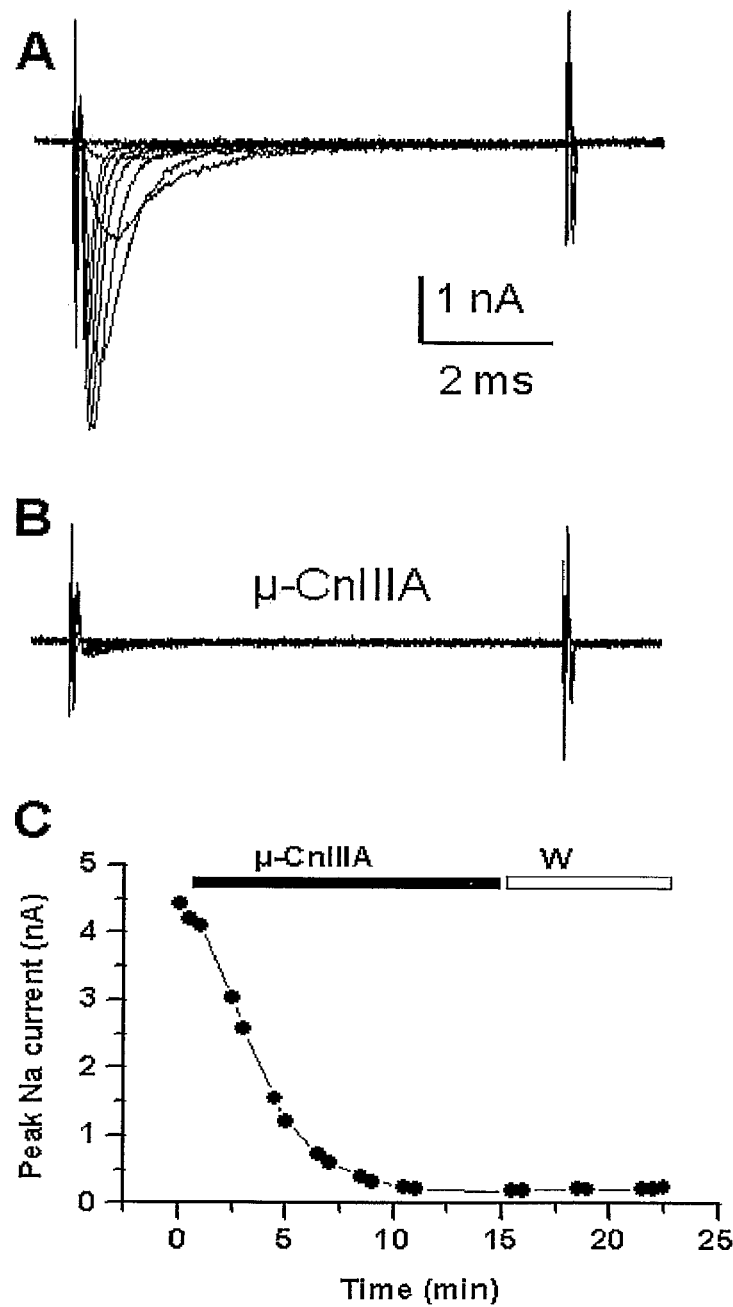

As shown in a typical experiment (FIG. 15), μ-CnIIIA (50 nM) applied by bath superfusion blocked sodium currents (FIGS. 15A and 15B) elicited by a family of depolarizing pulses from −100 to −10 mV. μ-CnIIIA blocked sodium current in a concentration-dependent manner as determined by sigmoidal nonlinear regression curve fitting for concentration-response data. The effective concentration that reduced 50% peak sodium current ($EC_{50}$) was 14.0 nM. As shown in FIG. 1C, washout began after peak sodium currents had reached a steady-state level in the presence of μ-CnIIIA did not reversed upon washing with a peptide-free medium. In contrast, STX action on sodium currents was completely reversed within 2-3 min perfusion with a STX-free solution. In typical experiments, μ-CnIIIA was persistent while STX effect was reversible upon washing out from the medium.

In Vivo Experiments on Mice—Digit Abduction Score (DAS) Assay

These experiments were performed on adult (between 2 and 3 months old) male or female Swiss-Webster mice (20-40 g). Each lightly anesthetized mouse received a single intramuscular injection of 50 or 100 μL physiological solution containing μ-CnIIIA or procaine into the antero-lateral region of the left hind limb. After the injection, functional recoveries were monitored by using the DAS assay (Aoki, 2001). Briefly, mice were suspended by the tail to elicit a characteristic startle response in which the animal extends its hind limbs and abducts its hind digits. Following μ-CnIIIA or procaine injection, the degree of digit abduction of the left and right hind limbs was determined as a function of time, and scored on a five-point scale (0=normal to 4=maximal reduction in digit abduction and leg extension) by an observer who was masked to treatment.

In Vivo Experiments on Mice—Grip Strength Assessment

Each lightly anesthetized mouse received a single intramuscular injection of 50 μL physiological solution containing μ-CnIIIA or procaine into the antero-lateral region of each front limb. Muscle strength was measured, before and at various times after the injection, using a grip strength meter for mice (600 g range; Technical and Scientific Equipment GmbH, Bad Homburg, Germany), connected to a laptop computer. The test was carried out essentially as originally described for rats (Tilson & Cabe, 1978). Briefly, mice were held on the base of the tail and allowed to firmly grab the pulling bar of the device with both forepaws. The mouse was then pulled gently backwards until it released its grip. The peak force of each trial was considered the grip strength. Each mouse performed three trials, which were about 30 s apart. The averaged value of the trials was expressed relatively to the corresponding control, and used for statistical analysis (mean±SEM of 2-3 mice).

The results (FIG. 12) show that a decrease of 50% of the relative strength occurred about 5 and 10 min after intramuscular injection of 108-111 pmoles μ-CnIIIA and 22-26 pmoles procaine per g of mouse, respectively. In addition of occurring about 2 times faster, the effect was also more pronounced in the presence of the peptide than in the presence of the local anaesthetic. Therefore, intramuscular injection of μ-CnIIIA is at least about 5000 fold more effective than procaine to produce, in vivo, a decrease of the muscle strength of mice.

Sodium Channel Expression

For expression in *X. laevis* oocytes, the Nav1.4/pUI-2 vectors were linearized with NotI and transcribed with the T7 mMESSAGE mMACHINE kit (Ambion).

Electrophysiological Studies on Cloned Channels

Oocytes were injected with 50 nl of cRNA at a concentration of 1 ng/nl using a microinjector from Drummond Scientific (Broomall, Pa.). The solution used for incubating the oocytes contained 96 mM NaCl, 2 mM KCl, 1.8 mM CaCl2, 2 mM MgCl2, and 5 mM HEPES, pH 7.4, supplemented with 50 mg/l gentamycin sulfate and 180 mg/l theophylline. Two-electrode voltage-clamp (TEVC) recordings were performed at room temperature (18-22° C.) using a GeneClamp 500 amplifier (Molecular Devices) controlled by a pClamp data acquisition system (Molecular Devices). Whole-cell currents from oocytes were recorded 1 day after injection. Voltage and current electrodes were filled with 3 M KCl. Resistances of both electrodes were kept as low as possible. Bath solution composition was 96 mM NaCl, 2 mM KCl, 1.8 mM CaCl2, 2 mM MgCl2, and 5 mM HEPES, pH 7.4. Currents were filtered at 1 kHz with a four-pole, low-pass Bessel filter and sampled at 5 kHz. Leak subtraction was performed using a −P/4 protocol. Currents were evoked in oocytes expressing the cloned Nav1.4 voltage gated sodium channel by depolarizations to the test potential of −10 mV for 100 ms from an holding potential of −90 mV. The pulse frequency was 0.2 Hz and the sampling frequency of 20 kHz. All experiments were carried out at room temperature.

The results shown in FIG. 14 demonstrate the ability of CnIIIA (500 nM) to block expressed Nav1.4 channels. From these experiments, it can be concluded that the peptide CnIIIA is able to block the voltage-gated sodium channel Nav1.4 isoform with an IC50 estimated in the range 1-50 nM. The peptide-channel interaction is compatible to a bimolecular reaction in which the association rate is concentration dependant. Finally, the reversibility of the effect has been noted as very low.

Example 3

CnIIIA Comparison with Other Mu-conotoxins

In Vitro Experiments on the Contraction of EDL Muscle of Mice

EDL muscles were isolated from mice killed by dislocation of the cervical vertebrae followed by immediate exsanguination. Isolated muscles were mounted in silicone-lined Plexiglass baths (4 ml volume) containing standard Krebs-Ringer physiological solution of the following composition (in mM): 154 NaCl; 5 KCl; 2 $CaCl_2$; 1 $MgCl_2$; 5 HEPES buffer (pH 7.4); 11 glucose. The solution was gassed with pure $O_2$.

For twitch tension measurements, one of the tendons of EDL muscle was tied with silk thread, via an adjustable stainless steel hook, to an FT03 isometric transducer (Grass Instruments, Astro-Med. Inc., West Warwick, R.I., USA), and the other tendon was pinned to the silicone-lined bath with stainless steel pins. Twitches were evoked by stimulating directly the muscle fibers by current pulses of 0.2 ms duration and supramaximal intensity, supplied by a S-44 stimulator (Grass Instruments, Astro-Med. Inc., West Warwick, R.I., USA) to an electrode array placed along the muscle, at frequencies of 0.1 Hz. For each preparation investigated, the resting tension was adjusted to obtain maximal contractile responses and was monitored during the whole duration of the experiment. Tension signals from the isometric transducer were amplified, collected, and digitized with the aid of a computer equipped with a DT2821 analogue to digital interface board (Data Translation, Marlboro, Mass., USA). Computerized data acquisition and analysis were performed with a program kindly provided by Dr. John Dempster (Department of Physiology & Pharmacology, University of Strathclyde, Glasgow, Scotland). All experiments were performed at 22° C. After preparations were equilibrated for 15 min with the oxygenated physiological solution containing 10 μM tubocurarine (to block nicotinic receptors), μ-conotoxins (CnIIIA, TIIIA, T3.1, PIIIA, SmIIIA, or SIIIA) were added to the medium.

To compare the relative effects of the different μ-conotoxins investigated on EDL muscles, a similar concentration (i.e. 100 nM) of μ-conotoxins was tested on muscle contraction. When possible, concentration-response curves were generated in individual muscles (the contraction measured in the presence of various concentrations of a given μ-conotoxin being expressed as percent of the control twitch response). Each μ-conotoxin concentration was applied by perfusion and allowed to equilibrate for 45-60 min. Sigmoidal nonlinear regression curve fitting for concentration-response data allowed an estimation of the effective concentration that reduces the twitch tension by 50% ($EC_{50}$).

Results (FIG. 13)

The relative mean contraction inhibition of the muscle is given for each peptide (100 nM) by comparison to CnIIIA (100 nM) after 40 min incubation. CnIIIA has been normalized to 100% for easy comparison. It can be noted that all peptides SmIIIA, PIIIA and T3.1 display a lower activity than CnIIIA (table below).

TABLE 2

| μ-conotoxin | Relative Mean % | SEM % | n |
|---|---|---|---|
| CnIIIA | 100.00 | 1.34 | 19 |
| SmIIIA | 83.00 | 0.85 | 11 |
| PIIIA | 50.00 | 3.70 | 11 |
| T3.1 | 3.30 | 1.12 | 12 |

Sigmoidal nonlinear regression curve fitting for concentration-response data allowed an estimation of the effective concentration that reduces the twitch tension by 50% ($EC_{50}$) and thus deduce the Kd (in nM) for each peptide. The results are presented in the table below:

TABLE 3

| μ-conotoxin | $K_D$ (nM) |
|---|---|
| CnIIIA | 125 |
| SmIIIA | 130 |
| PIIIA | 500 |
| T3.1 | 800 |

Summary of Published Mu-Conopeptide Sequences in the Literature Vs CnIIIA [SEQ ID No 2]

TABLE 4

| Name | Sequence | Homology (%) | Reference |
|---|---|---|---|
| CnIIIA | Z G C C N G P K G C S S K W C R D H A R C C * | | |
| GIIIA | R D C C T O O K K C K D R Q C K O Q - R C C A * | 45 | Sato et al., 1983 |
| GIIIB | R D C C T O O R K C K D R R C K O M - K C C A * | 45 | Sato et al., 1983 |
| GIIIC | R D C C T O O K K C K D R R C K O L - K C C A * | 45 | Cruz et al., 1985 |
| PIIIA | Z R L C C G F O K S C R S R Q C K O H - R C C * | 60 | Shon et al., 1998 |
| SmIIIA | Z R C C N G R R G C S S R W C R D H S R C C * | 86 | West et al., 2002 |
| SIIIA | Z N C C N G - - G C S S K W C R D H A R C C * | 86 | Bulaj et al., 2005 |
| KIIIA | C C N - - - - C S S K W C R D H S R C C * | 68 | Bulaj et al., 2005 |

Z and O stand for pyroglutamic acid and hydroxyproline residues respectively; *denotes C-terminal amidation; The bent lines display the disulfide pairing.
The listed sequences have the following SEQ ID NO designations: CnIIIA = SEQ ID NO:2; GIIIA = SEQ ID NO:4; GIIIB = SEQ ID NO:5; GIIIC = SEQ ID NO:6; PIIIA = SEQ ID NO:7; SmIIIA = SEQ ID NO:8; SIIIA = SEQ ID NO:9; and KIIIA = SEQ ID NO:10.

REFERENCE LIST

Amblard M. et al, 2005, Methods Mol Biol. 298, 3-24

Baker, M. D. and Wood, J. N., 2001. Involvement of Na+ channels in pain pathways. Trends Pharmacol. Sci. 1 (22), 27-31.

Becker, S., Atherton, E., Gordon, R. D., 1989. Synthesis and characterization of mu-conotoxin IIIa. Eur. J. Biochem. 1 (185), 79-84.

Benoit, E., Charpentier G, Mateu L, Luzzati V, Kado R, 2000. The pike olfactory nerve: a source of unmyelinated sensory axons. Cybium, Rev. Eur. Ichtyol. 3 (24), 241-248.

Bulaj, G., West, P. J., Garrett, J. E., Marsh, M., Zhang, M. M., Norton, R. S., Smith, B. J., Yoshikami, D., Olivera, B. M., 2005. Novel conotoxins from Conus striatus and Conus kinoshitai selectively block TTX-resistant sodium channels. Biochemistry 19 (44), 7259-7265.

Cruz, L. J., Gray, W. R., Olivera, B. M., Zeikus, R. D., Kerr, L., Yoshikami, D., Moczydlowski, E., 1985. Conus geographus toxins that discriminate between neuronal and muscle sodium channels. J. Biol. Chem. 16 (260), 9280-9288.

Cruz, L. J., Kupryszewski, G., LeCheminant, G. W., Gray, W. R., Olivera, B. M., Rivier, J., 1989. mu-conotoxin GIIIA, a peptide ligand for muscle sodium channels: chemical synthesis, radiolabeling, and receptor characterization. Biochemistry 8 (28), 3437-3442.

Decosterd, I., Ji, R. R., Abdi, S., Tate, S., Woolf, C. J., 2002. The pattern of expression of the voltage-gated sodium channels Na(v)1.8 and Na(v)1.9 does not change in uninjured primary sensory neurons in experimental neuropathic pain models. Pain 3 (96), 269-277.

Fainzilber, M., Kofman, O., Zlotkin, E., Gordon, D., 1994. A new neurotoxin receptor site on sodium channels is identified by a conotoxin that affects sodium channel inactivation in molluscs and acts as an antagonist in rat brain. J. Biol. Chem. 4 (269), 2574-2580.

Fainzilber, M., Nakamura, T., Gaathon, A., Lodder, J. C., Kits, K. S., Burlingame, A. L., Zlotkin, E., 1995. A new cysteine framework in sodium channel blocking conotoxins. Biochemistry 27 (34), 8649-8656.

Finucane B. T., 2005. Allergies to local anesthetics—the real truth. 50:869-874. Canadian Journal of Anesthesia (50), 869-874.

French, R. J., Prusak-Sochaczewski, E., Zamponi, G. W., Becker, S., Kularatna, A. S., Horn, R., 1996. Interactions between a pore-blocking peptide and the voltage sensor of the sodium channel: an electrostatic approach to channel geometry. Neuron 2 (16), 407-413.

Gold, M. S., Weinreich, D., Kim, C. S., Wang, R., Treanor, J., Porreca, F., Lai, J., 2003. Redistribution of Na(V)1.8 in uninjured axons enables neuropathic pain. J. Neurosci. 1 (23), 158-166.

Hill, J. M., Alewood, P. F., Craik, D. J., 1996. Three-dimensional solution structure of mu-conotoxin GIIIB, a specific blocker of skeletal muscle sodium channels. Biochemistry 27 (35), 8824-8835.

Julius, D. and Basbaum, A. I., 2001. Molecular mechanisms of nociception. Nature 6852 (413), 203-210.

Keizer, D. W., West, P. J., Lee, E. F., Yoshikami, D., Olivera, B. M., Bulaj, G., Norton, R. S., 2003. Structural basis for tetrodotoxin-resistant sodium channel binding by mu-conotoxin SmIIIA. J. Biol. Chem. 47 (278), 46805-46813.

Kerr, L. M. and Yoshikami, D., 1984. A venom peptide with a novel presynaptic blocking action. Nature 5956 (308), 282-284.

Lee, A. G., 1976. Model for action of local anaesthetics. Nature 5569 (262), 545-548.

McIntosh, J. M., Olivera, B. M., Cruz, L. J., 1999. Conus peptides as probes for ion channels. Methods Enzymol. (294), 605-624.

Moczydlowski, E., Olivera, B. M., Gray, W. R., Strichartz, G. R., 1986. Discrimination of muscle and neuronal Na-channel subtypes by binding competition between [3H] saxitoxin and mu-conotoxins. Proc. Natl. Acad. Sci. U.S.A 14 (83), 5321-5325.

Nielsen, K. J., Watson, M., Adams, D. J., Hammarstrom, A. K., Gage, P. W., Hill, J. M., Craik, D. J., Thomas, L., Adams, D., Alewood, P. F., Lewis, R. J., 2002. Solution structure of mu-conotoxin PIIIA, a preferential inhibitor of persistent tetrodotoxin-sensitive sodium channels. J. Biol. Chem. 30 (277), 27247-27255.

Olivera, B. M., Cruz, L. J., de, S., V, LeCheminant, G. W., Griffin, D., Zeikus, R., McIntosh, J. M., Galyean, R., Varga, J., Gray, W. R., 1987. Neuronal calcium channel antagonists. Discrimination between calcium channel subtypes using omega-conotoxin from *Conus magus* venom. Biochemistry 8 (26), 2086-2090.

Olivera, B. M., Gray, W. R., Zeikus, R., McIntosh, J. M., Varga, J., Rivier, J., de, S., V, Cruz, L. J., 1985. Peptide neurotoxins from fish-hunting cone snails. Science 4732 (230), 1338-1343.

Olivera, B. M., McIntosh, J. M., Cruz, L. J., Luque, F. A., Gray, W. R., 1984. Purification and sequence of a presynaptic peptide toxin from *Conus geographus* venom. Biochemistry 22 (23), 5087-5090.

Olivera, B. M., Rivier, J., Clark, C., Ramilo, C. A., Corpuz, G. P., Abogadie, F. C., Mena, E. E., Woodward, S. R., Hillyard, D. R., Cruz, L. J., 1990. Diversity of *Conus* neuropeptides. Science 4966 (249), 257-263.

Ott, K. H., Becker, S., Gordon, R. D., Ruterjans, H., 1991. Solution structure of mu-conotoxin GIIIA analysed by 2D-NMR and distance geometry calculations. FEBS Lett. 2 (278), 160-166.

Safo, P., Rosenbaum, T., Shcherbatko, A., Choi, D. Y., Han, E., Toledo-Aral, J. J., Olivera, B. M., Brehm, P., Mandel, G., 2000. Distinction among neuronal subtypes of voltage-activated sodium channels by mu-conotoxin PIIIA. J. Neurosci. 1 (20), 76-80.

Sato, K., Ishida, Y., Wakamatsu, K., Kato, R., Honda, H., Ohizumi, Y., Nakamura, H., Ohya, M., Lancelin, J. M., Kohda, D., 1991. Active site of mu-conotoxin GIIIA, a peptide blocker of muscle sodium channels. J. Biol. Chem. 26 (266), 16989-16991.

Sato, S., Nakamura, H., Ohizumi, Y., Kobayashi, J., Hirata, Y., 1983. The amino acid sequences of homologous hydroxyproline-containing myotoxins from the marine snail *Conus geographus* venom. FEBS Lett. 2 (155), 277-280.

Scholz, A., 2002. Mechanisms of (local) anaesthetics on voltage-gated sodium and other ion channels. Br. J. Anaesth. 1 (89), 52-61.

Shichor, I., Fainzilber, M., Pelhate, M., Malecot, C. O., Zlotkin, E., Gordon, D., 1996. Interactions of delta-conotoxins with alkaloid neurotoxins reveal differences between the silent and effective binding sites on voltage-sensitive sodium channels. J. Neurochem. 6 (67), 2451-2460.

Shon, K. J., Olivera, B. M., Watkins, M., Jacobsen, R. B., Gray, W. R., Floresca, C. Z., Cruz, L. J., Hillyard, D. R., Brink, A., Terlau, H., Yoshikami, D., 1998. mu-Conotoxin PIIIA, a new peptide for discriminating among tetrodotoxin-sensitive Na channel subtypes. J. Neurosci. 12 (18), 4473-4481.

Wakamatsu, K., Kohda, D., Hatanaka, H., Lancelin, J. M., Ishida, Y., Oya, M., Nakamura, H., Inagaki, F., Sato, K., 1992. Structure-activity relationships of mu-conotoxin GIIIA: structure determination of active and inactive sodium channel blocker peptides by NMR and simulated annealing calculations. Biochemistry 50 (31), 12577-12584.

West, P. J., Bulaj, G., Garrett, J. E., Olivera, B. M., Yoshikami, D., 2002. Mu-conotoxin SmIIIA, a potent inhibitor of tetrodotoxin-resistant sodium channels in amphibian sympathetic and sensory neurons. Biochemistry 51 (41), 15388-15393.

Yu, F. H. and Catterall, W. A., 2003. Overview of the voltage-gated sodium channel family. Genome Biol. 3 (4), 207

The invention claimed is:

1. A pharmaceutical composition comprising a pharmaceutically acceptable carrier and an effective amount of an isolated and purified mu-conotoxin peptide consisting of the amino acid sequence: Xaa1-Xaa2-Cys-Cys-Xaa3-Xaa4-Xaa5-Xaa6-Xaa7-Cys-Xaa8-Xaa9-Xaa10-Xaa11-Cys-Xaa12-Xaa13-Xaa14-Xaa15-Xaa16-Cys-Cys-Xaa17 [SEQ ID NO:1], wherein Xaa1 is any N-modified amino acid, Xaa2 is glycine, Xaa3 is absent or is any acidic amino acid or any of its amide form, Xaa4 is absent or is glycine, Xaa5 is absent or is proline or hydroxy-proline, Xaa6 is absent or is any basic amino acid, Xaa7 is absent or is glycine, Xaa8 is absent or is any non-aromatic hydroxyl amino acid, Xaa9 is absent or is any non-aromatic hydroxyl amino acid, Xaa10 is absent or is any basic amino acid, Xaa11 is absent or is any aromatic amino acid, Xaa12 is absent or is any basic amino acid, Xaa13 is absent or is any acidic amino acid or any of its amide form, Xaa14 is absent or is any basic amino acid, or any sulfur-containing amino acid, Xaa15 is absent or is any hydrophobic or apolar amino acid, or any non-aromatic hydroxyl amino acid, Xaa16 is absent or is any basic amino acid, Xaa17 is absent or is any apolar amino acid, or an amide group, wherein the isolated and purified mu-conotoxin peptide is the only conotoxin peptide of *Conus consors* in the pharmaceutical composition.

2. The pharmaceutical composition of claim 1, wherein at least one amino acid selected from the group consisting of amino acids Xaa3 , Xaa4, Xaa5, Xaa6 and Xaa7 is absent.

3. The pharmaceutical composition of claim 1, wherein at least one amino acid selected from the group consisting of amino acids Xaa8 , Xaa9, Xaa10 and Xaa11 is absent.

4. The pharmaceutical composition of claim 1, wherein at least one amino acid selected from the group consisting of amino acids Xaa12, Xaa13, Xaa14, Xaa15 and Xaa16 is absent.

5. The pharmaceutical composition of claim 1, wherein the N-modification of amino-acid Xaa1 is selected from the group consisting of acetylation, formylation, myristoylation and amidation;

Xaa3 and Xaa13 are independently selected from the group consisting of aspartic acid (Asp), asparagine (Asn), glutamic acid (Glu), glutamine (Gln) and pyroglutamic acid (pGlu or Z);

Xaa6, Xaa10, Xaa12 and Xaa16 are independently selected from the group consisting of arginine (Arg), lysine (Lys) and histidine (His);

Xaa8 and Xaa9 are independently selected from the group consisting of serine (Ser) and threonine (Thr);

Xaa11 is selected from the group consisting of phenylalanine (Phe), tyrosine (Tyr), and tryptophan (Trp);

Xaa14 is selected from the group consisting of arginine (Arg), lysine (Lys), histidine (His), cysteine (Cys) and methionine (Met);

Xaa15 is selected from the group consisting of glycine (Gly), alanine (Ala), valine (Val), leucine (Leu), isoleucine (Ile), serine (Ser), threonine (Thr), methionine (Met), cysteine (Cys) and proline (Pro);

Xaa17 is selected from the group consisting of glycine (Gly), alanine (Ala), valine (Val), leucine (Leu), isoleucine (Ile), threonine (Thr), methionine (Met), phenylalanine (Phe) and proline (Pro).

6. The pharmaceutical composition of claim 1, wherein Xaa1 is pyroglutamate (pGlu).

7. The pharmaceutical composition of claim 1, wherein the amino acid sequence is pGlu-Gly-Cys-Cys-Asn-Gly-Pro-Lys-Gly-Cys-Ser-Ser-Lys-Trp-Cys-Arg-Asp-His-Ala-Arg-Cys-Cys [SEQ ID NO: 2].

8. A method of treating pain, the method comprising administering the pharmaceutical composition of claim 1 to a subject in need thereof.

9. The method of claim 8, wherein the pain is selected from the group consisting of migraine, acute pain, persistent pain, chronic pain, neuropathic pain and nociceptive pain.

10. A method for the treatment of a disorder associated with voltage-sensitive sodium channels in a subject in need thereof, the method comprising administering a pharmaceutically effective amount of the pharmaceutical composition of claim 1 to the subject.

11. The method according to claim 10, wherein the voltage-sensitive sodium channels are Nav1.4 channels.

12. A method for providing anesthesia to a subject in need thereof, the method comprising administering a pharmaceutically effective amount of the pharmaceutical composition of claim 1 to the subject.

13. A method for providing musculoskeletal relaxation in a patient undergoing a surgical procedure requiring anesthesia which comprises administering to the patient the pharmaceutical composition of claim 1.

14. The method of claim 13, wherein the pharmaceutical composition is administered as an ocular anesthetic.

15. The method of claim 13, wherein the pharmaceutical composition is administered as a local anesthetic.

16. The method of claim 13 having an anesthetic effect comprised between about 30 min to 48 hours.

17. A method for local anesthesia, the method comprising administering the pharmaceutical composition of claim 1 to a subject in need thereof.

18. The method for local anesthesia of claim 17, having an anesthetic effect comprised between about 30 min to 48 hours.

19. A method for the treatment of a pain in a subject in need thereof, the method comprising administering the pharmaceutical composition of claim 1 to the subject.

20. The method of claim 19, having an effect comprised between about 30 min to 12 hours.

21. An anesthetic comprising the pharmaceutical composition of claim 1.

22. The anesthetic of claim 21, wherein said anesthetic is suitable for subcutaneous, intravenous, intradermal, intramuscular, intraperitoneal, intranasal, transdermal, or buccal routes of application.

23. The anesthetic of claim 21, wherein it is in the form of tablets, capsules, lozenges, dental pastes, suppositories, inhalants, solutions, ointments, creams or parenteral depots.

24. The anesthetic of claim 23, wherein the inhalant is a spray.

25. An implantable device comprising the pharmaceutical composition of claim 1.

26. The pharmaceutical composition of claim 1, wherein the composition is adapted for topical administration.

27. A sterile composition comprising an effective amount of an isolated and purified mu-conotoxin peptide consisting of SEQ ID NO:1, wherein Xaa1 is any N-modified amino acid,
Xaa2 is glycine,
Xaa3 is absent or is any acidic amino acid or any of its amide form,
Xaa4 is absent or is glycine,
Xaa5 is absent or is proline or hydroxy-proline,
Xaa6 is absent or is any basic amino acid,
Xaa7 is absent or is glycine,
Xaa8 is absent or is any non-aromatic hydroxyl amino acid,
Xaa9 is absent or is any non-aromatic hydroxyl amino acid,
Xaa10 is absent or is any basic amino acid,
Xaa11 is absent or is any aromatic amino acid,
Xaa12 is absent or is any basic amino acid,
Xaa13 is absent or is any acidic amino acid or any of its amide form,
Xaa14 is absent or is any basic amino acid, or any sulfur-containing amino acid,
Xaa15 is absent or is any hydrophobic or apolar amino acid, or any non-aromatic hydroxyl amino acid,
Xaa16 is absent or is any basic amino acid,
Xaa17 is absent or is any apolar amino acid, or an amide group,
wherein the isolated and purified mu-conotoxin peptide is the only conotoxin peptide of *Conus consors* in the sterile composition.

28. A salt of an isolated and purified mu-conotoxin peptide consisting of the amino acid sequence: Xaa1-Xaa2-Cys-Cys-Xaa3-Xaa4-Xaa5-Xaa6-Xaa7-Cys-Xaa8-Xaa9-Xaa10-Xaa11-Cys-Xaa12 -Xaa13-Xaa14-Xaa15-Xaa16-Cys-Cys-Xaa17 [SEQ ID NO:1], wherein Xaa1 is any N-modified amino acid,
Xaa2 is glycine,
Xaa3 is absent or is any acidic amino acid or any of its amide form,
Xaa4 is absent or is glycine,
Xaa5 is absent or is proline or hydroxy-proline,
Xaa6 is absent or is any basic amino acid,
Xaa7 is absent or is glycine,
Xaa8 is absent or is any non-aromatic hydroxyl amino acid,
Xaa9 is absent or is any non-aromatic hydroxyl amino acid,
Xaa10 is absent or is any basic amino acid,
Xaa11 is absent or is any aromatic amino acid,
Xaa12 is absent or is any basic amino acid,
Xaa13 is absent or is any acidic amino acid or any of its amide form,
Xaa14 is absent or is any basic amino acid, or any sulfur-containing amino acid, Xaa15 is absent or is any hydrophobic or apolar amino acid, or any non-aromatic hydroxyl amino acid, Xaa16 is absent or is any basic amino acid, Xaa17 is absent or is any apolar amino acid, or an amide group,and wherein the isolated and purified mu-conotoxin peptide is not admixed with any other conotoxin peptide.

29. The salt of a peptide of claim 28, wherein the salt is an acetate salt.

30. A pharmaceutical composition comprising the salt of a peptide of claim 28.

31. The pharmaceutical composition of claim 1, wherein the pharmaceutical composition is effective to provide musculoskeletal relaxation.

32. The pharmaceutical composition of claim 31, wherein the pharmaceutical composition is effective to inhibit skeletal muscle contraction.

33. The pharmaceutical composition of claim 32, wherein the pharmaceutical composition is effective to inhibit skeletal muscle contraction without altering nerve membrane excitability.

* * * * *